US012188875B2

(12) United States Patent
Aikawa

(10) Patent No.: US 12,188,875 B2
(45) Date of Patent: Jan. 7, 2025

(54) COMPONENT MEASUREMENT APPARATUS, COMPONENT MEASUREMENT APPARATUS SET, AND INFORMATION PROCESSING METHOD

(71) Applicant: TERUMO KABUSHIKI KAISHA, Tokyo (JP)

(72) Inventor: Ryokei Aikawa, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 269 days.

(21) Appl. No.: 17/888,010

(22) Filed: Aug. 15, 2022

(65) Prior Publication Data

US 2022/0390380 A1    Dec. 8, 2022

Related U.S. Application Data

(63) Continuation of application No. PCT/JP2021/000119, filed on Jan. 5, 2021.

(30) Foreign Application Priority Data

Feb. 20, 2020   (JP) .................................. 2020-027564

(51) Int. Cl.
*G01N 21/78*   (2006.01)
*G01N 21/3577*   (2014.01)
(Continued)

(52) U.S. Cl.
CPC ......... *G01N 21/78* (2013.01); *G01N 21/3577* (2013.01); *G01N 21/51* (2013.01);
(Continued)

(58) Field of Classification Search
CPC .... G01N 21/78; G01N 21/3577; G01N 21/51; G01N 21/8483; G01N 33/49;
(Continued)

(56) References Cited

U.S. PATENT DOCUMENTS

2003/0060692 A1   3/2003  Ruchti et al.
2013/0200140 A1   8/2013  Kawabata et al.
(Continued)

FOREIGN PATENT DOCUMENTS

CN    209992426 U    1/2020
JP    2005-055290 A    3/2005
(Continued)

OTHER PUBLICATIONS

English machine Translation of JP2017124040 (Year: 2017).*
(Continued)

*Primary Examiner* — Dominic J Bologna
(74) *Attorney, Agent, or Firm* — Foley & Lardner LLP

(57) ABSTRACT

A component measurement apparatus includes: a chip insertion space for inserting a component measurement chip provided with a reagent that reacts with a component to be measured in a sample; a light emitting unit configured to emit radiation light to the component measurement chip in a state in which the component measurement chip is inserted into the chip insertion space; a light receiving unit configured to receive light transmitted through or reflected from the component measurement chip; and a control unit configured to determine whether there is a possibility that an incorrect processing mode has been selected for execution.

12 Claims, 17 Drawing Sheets

(51) Int. Cl.
- *G01N 21/51* (2006.01)
- *G01N 21/77* (2006.01)
- *G01N 21/84* (2006.01)
- *G01N 33/49* (2006.01)
- *G01N 33/66* (2006.01)
- *G01N 33/72* (2006.01)

(52) U.S. Cl.
CPC ......... *G01N 21/8483* (2013.01); *G01N 33/49* (2013.01); *G01N 33/66* (2013.01); *G01N 33/721* (2013.01); *G01N 2021/7773* (2013.01); *G01N 2201/12723* (2013.01)

(58) Field of Classification Search
CPC ................. G01N 33/66; G01N 33/721; G01N 2021/7773; G01N 2201/12723
See application file for complete search history.

(56) References Cited

U.S. PATENT DOCUMENTS

| | | | |
|---|---|---|---|
| 2017/0102336 A1* | 4/2017 | Takinami | G01N 21/8483 |
| 2019/0011371 A1* | 1/2019 | Aikawa | G01N 21/31 |
| 2020/0011806 A1 | 1/2020 | Aikawa | |

FOREIGN PATENT DOCUMENTS

| | | | |
|---|---|---|---|
| JP | 2009-270899 A | | 11/2009 |
| JP | 2011-064596 A | | 3/2011 |
| JP | 2014-190926 A | | 10/2014 |
| JP | 2015-169512 A | | 9/2015 |
| JP | 2017124040 A | * | 7/2017 |
| JP | 2019-045147 A | | 3/2019 |
| WO | WO-2014/045346 A1 | | 3/2014 |
| WO | WO-2018/173609 A1 | | 9/2018 |

OTHER PUBLICATIONS

International Searching Authority, "International Search Report," issued in connection with International Patent Application No. PCT/JP2021/000119, dated Apr. 6, 2021.

International Searching Authority, "Written Opinion," issued in connection with International Patent Application No. PCT/JP2021/000119, dated Apr. 6, 2021.

International Searching Authority, "Written Opinion," issued in connection with International Patent Application No. PCT/JP2021/000119, dated Apr. 6, 2021 with English translation (6 pages).

Extended European Search Report issued in connection with EP Appl. Ser. No. 21757836.8 dated Dec. 7, 2022.

* cited by examiner

[FIG. 1]
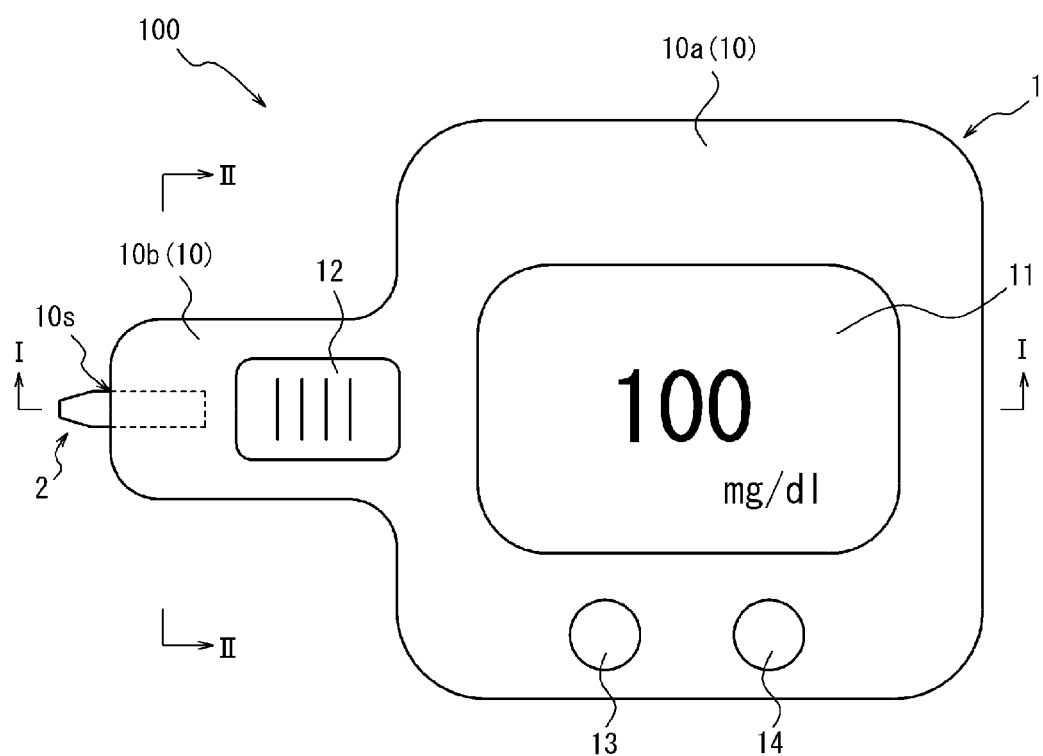

[FIG. 2]
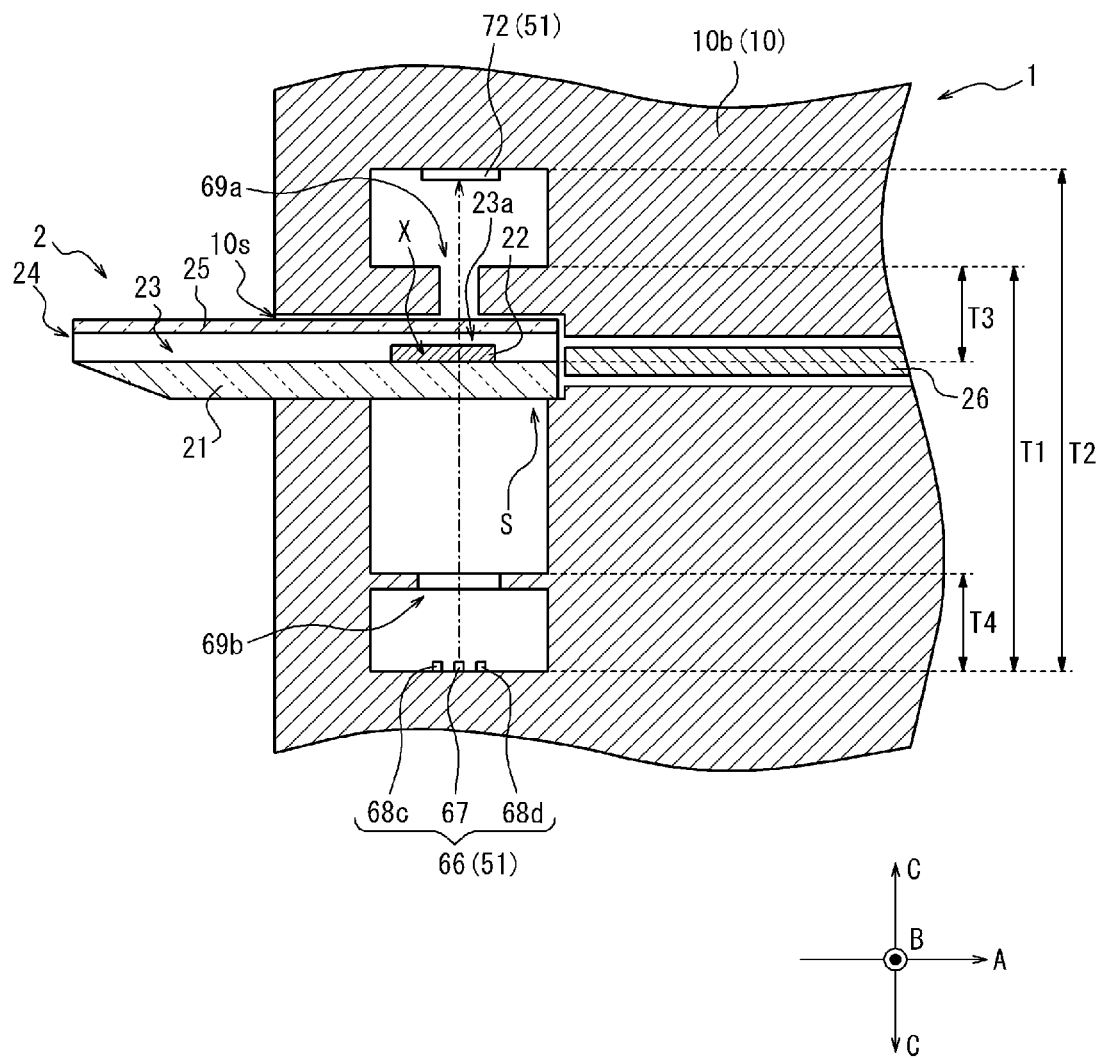

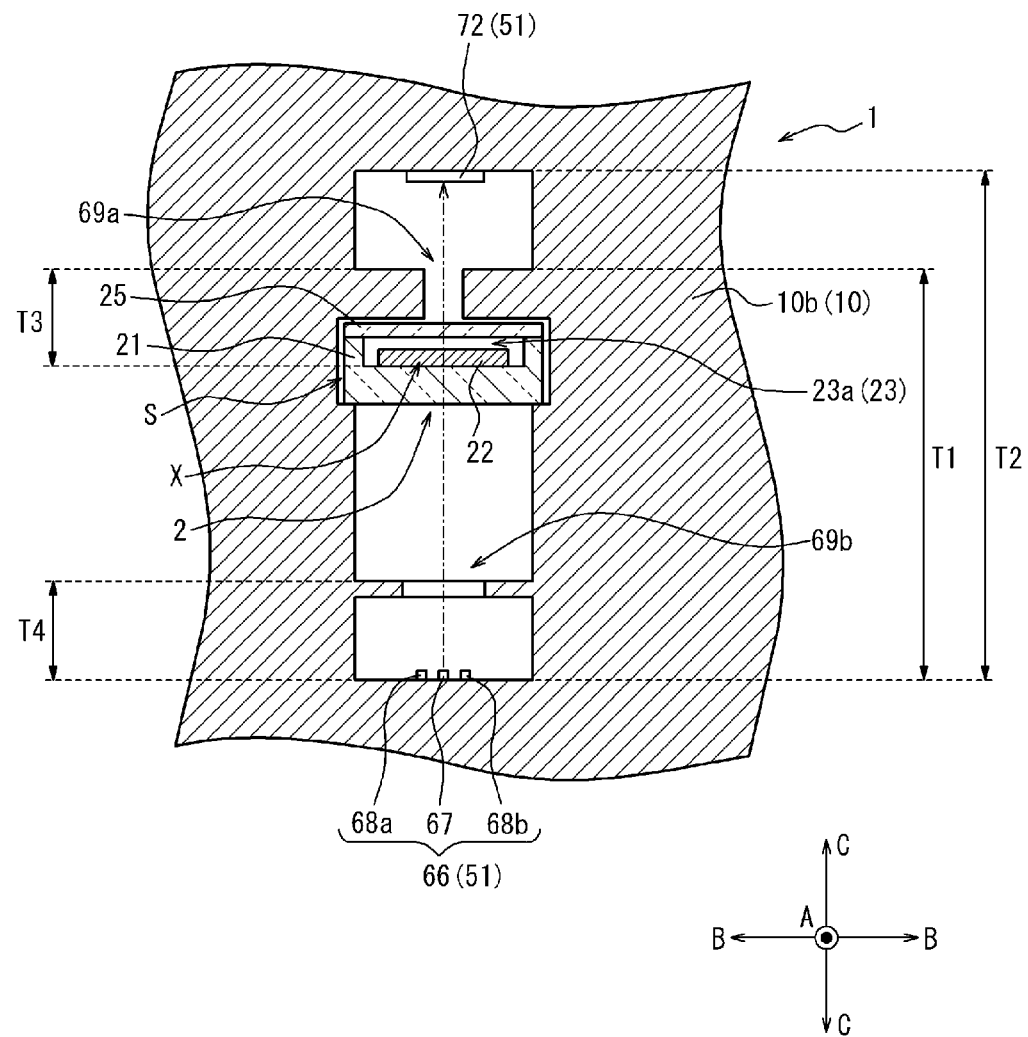
[FIG. 3]

[FIG. 4]
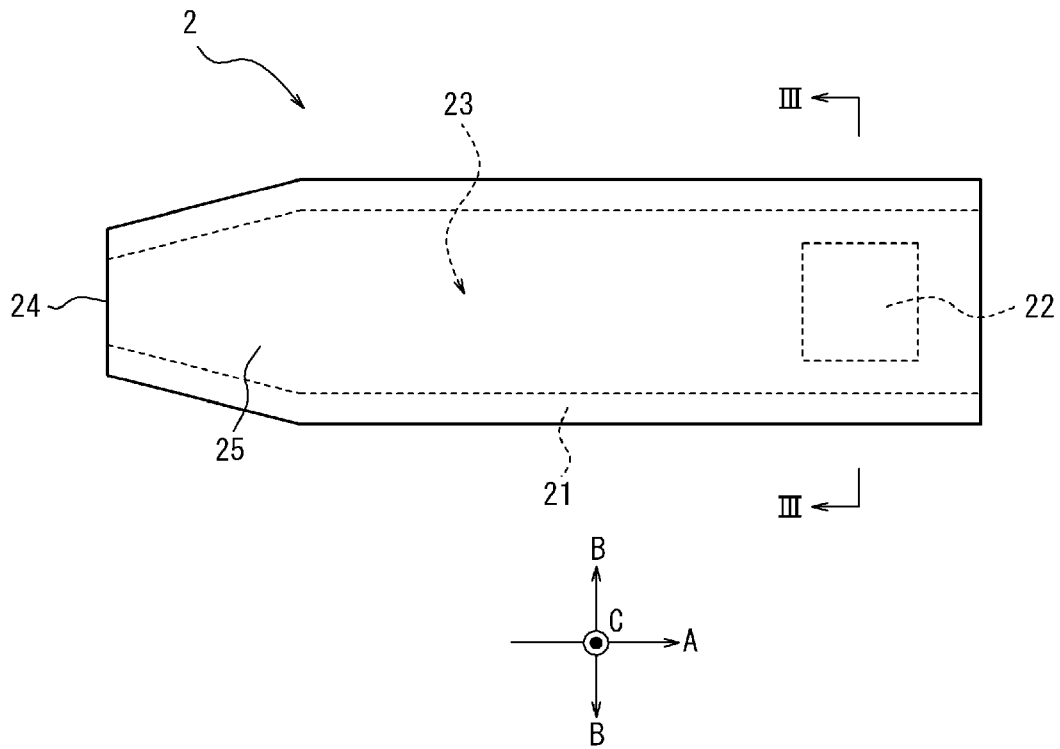
[FIG. 5]
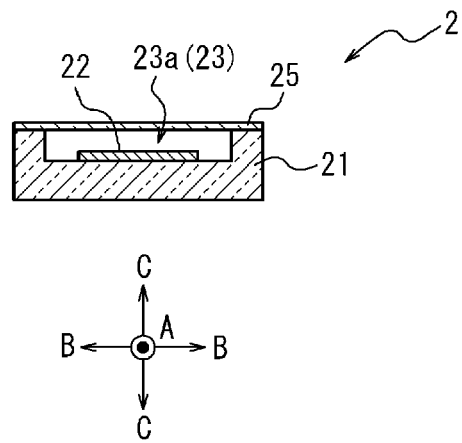

[FIG. 6]
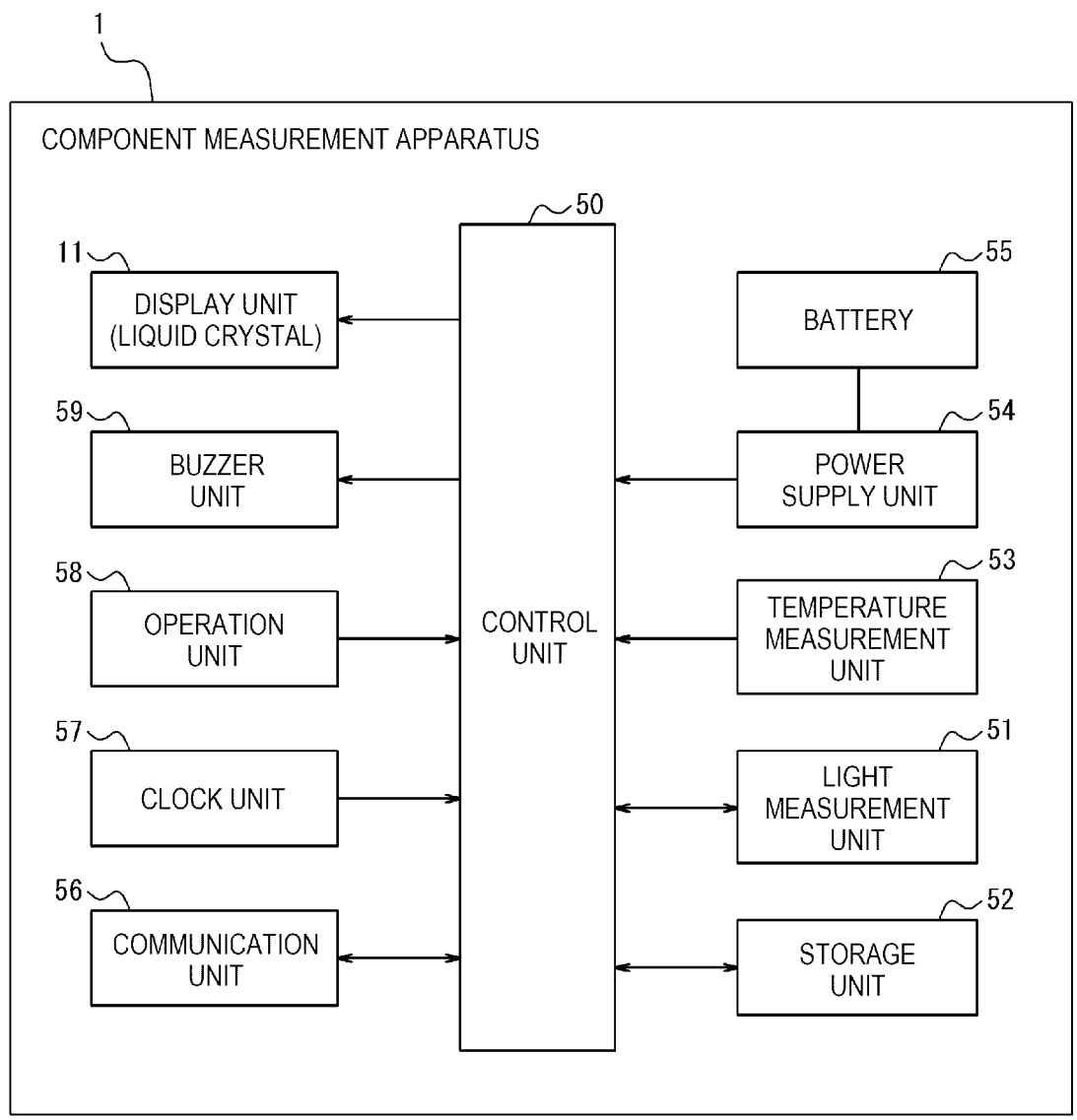

[FIG. 7]
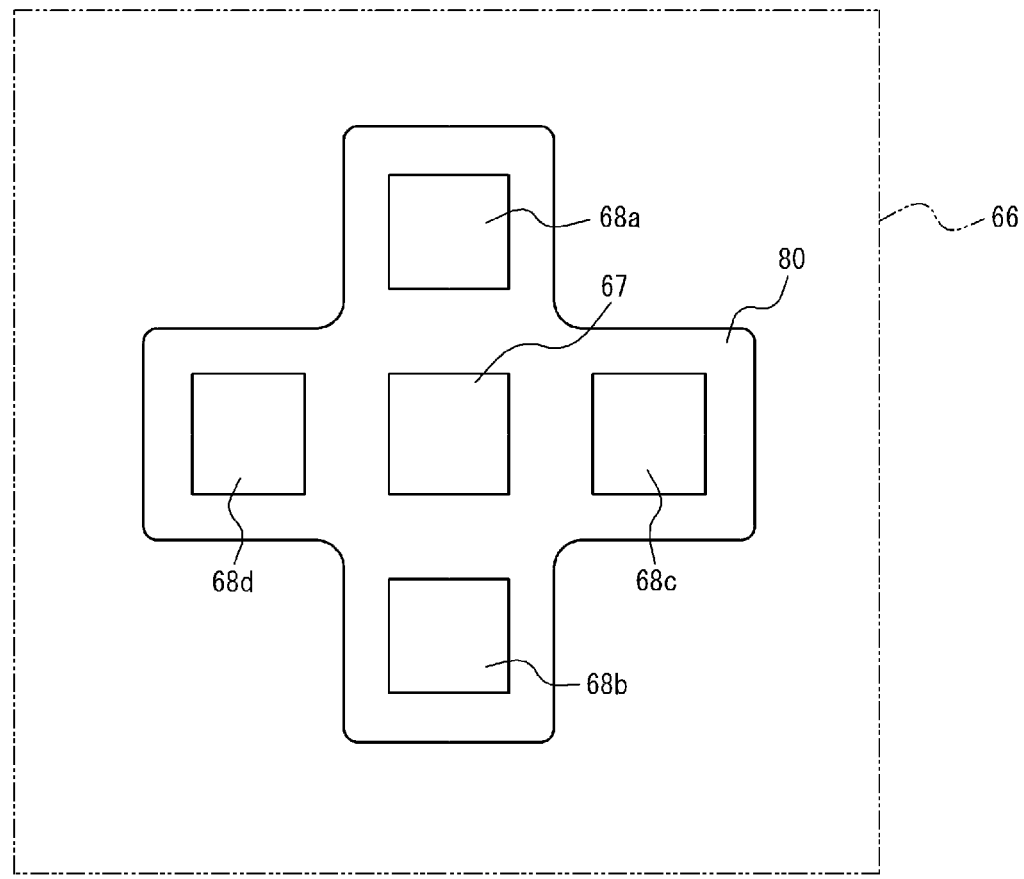
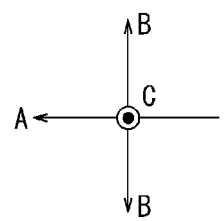

[FIG. 8]
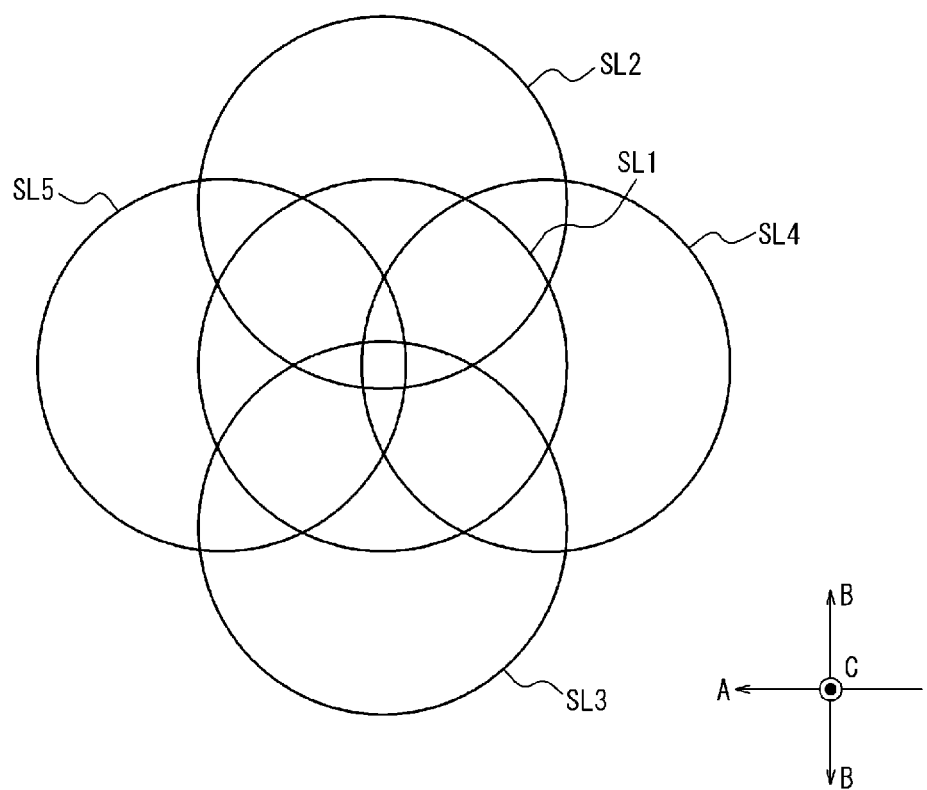

[FIG. 9]
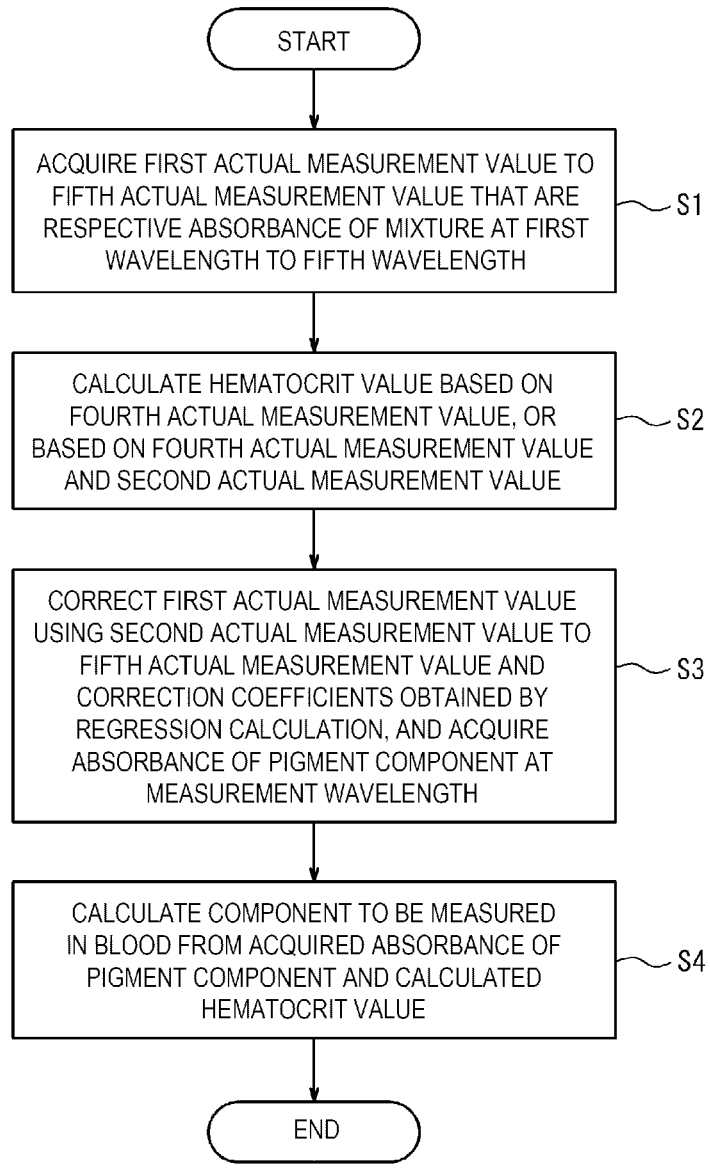

[FIG. 10]
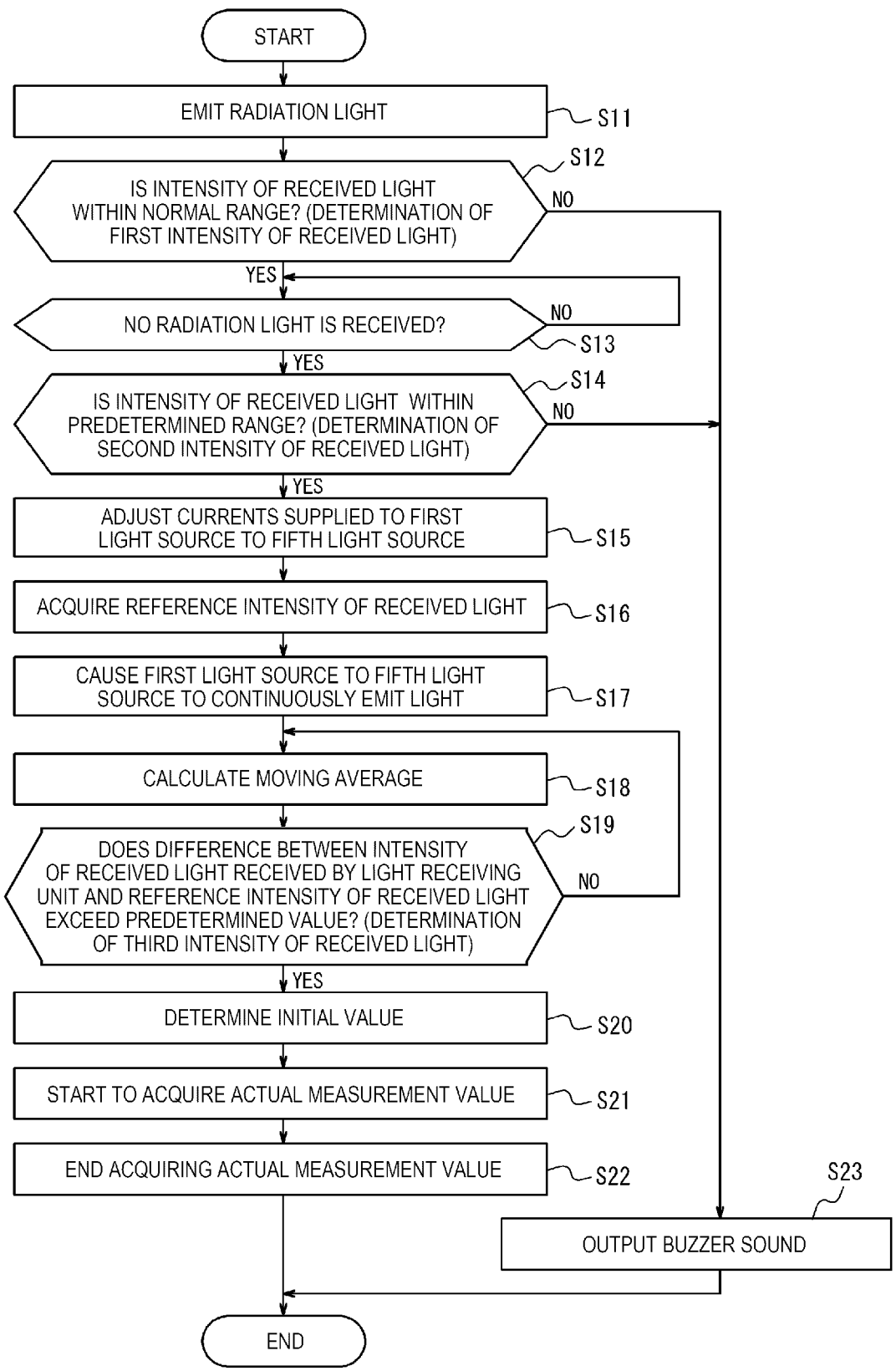

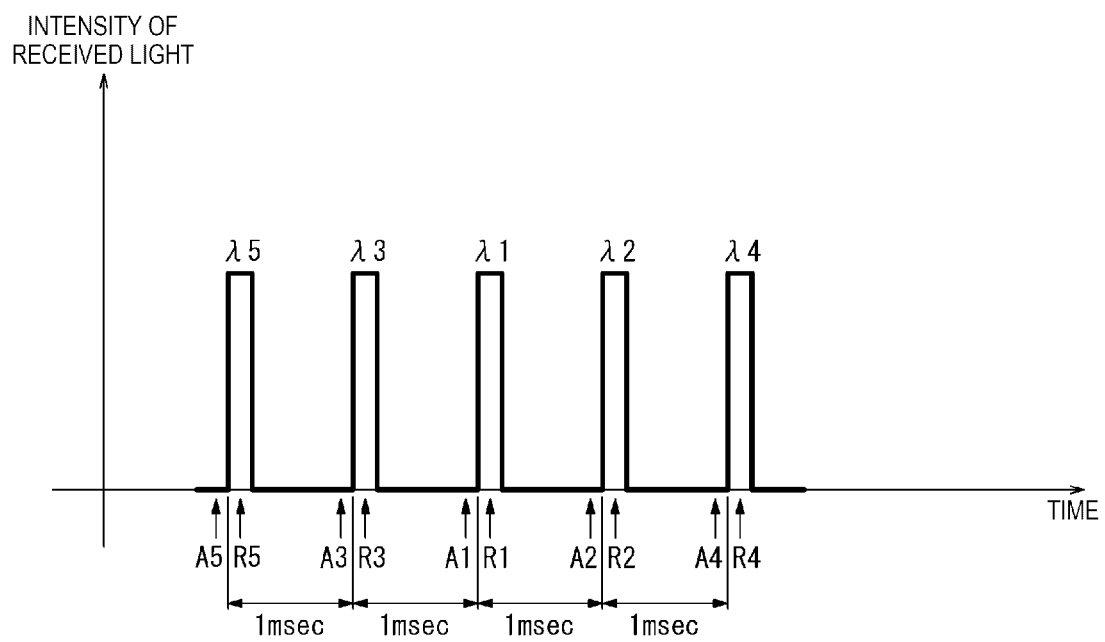
[FIG. 11]

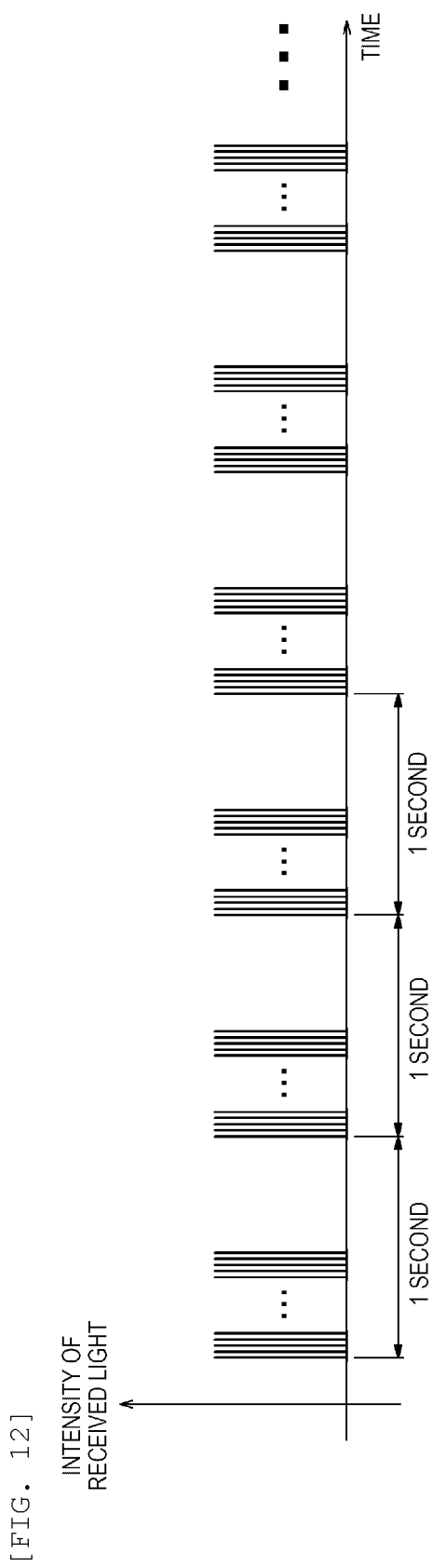
[FIG. 12]

[FIG. 13]
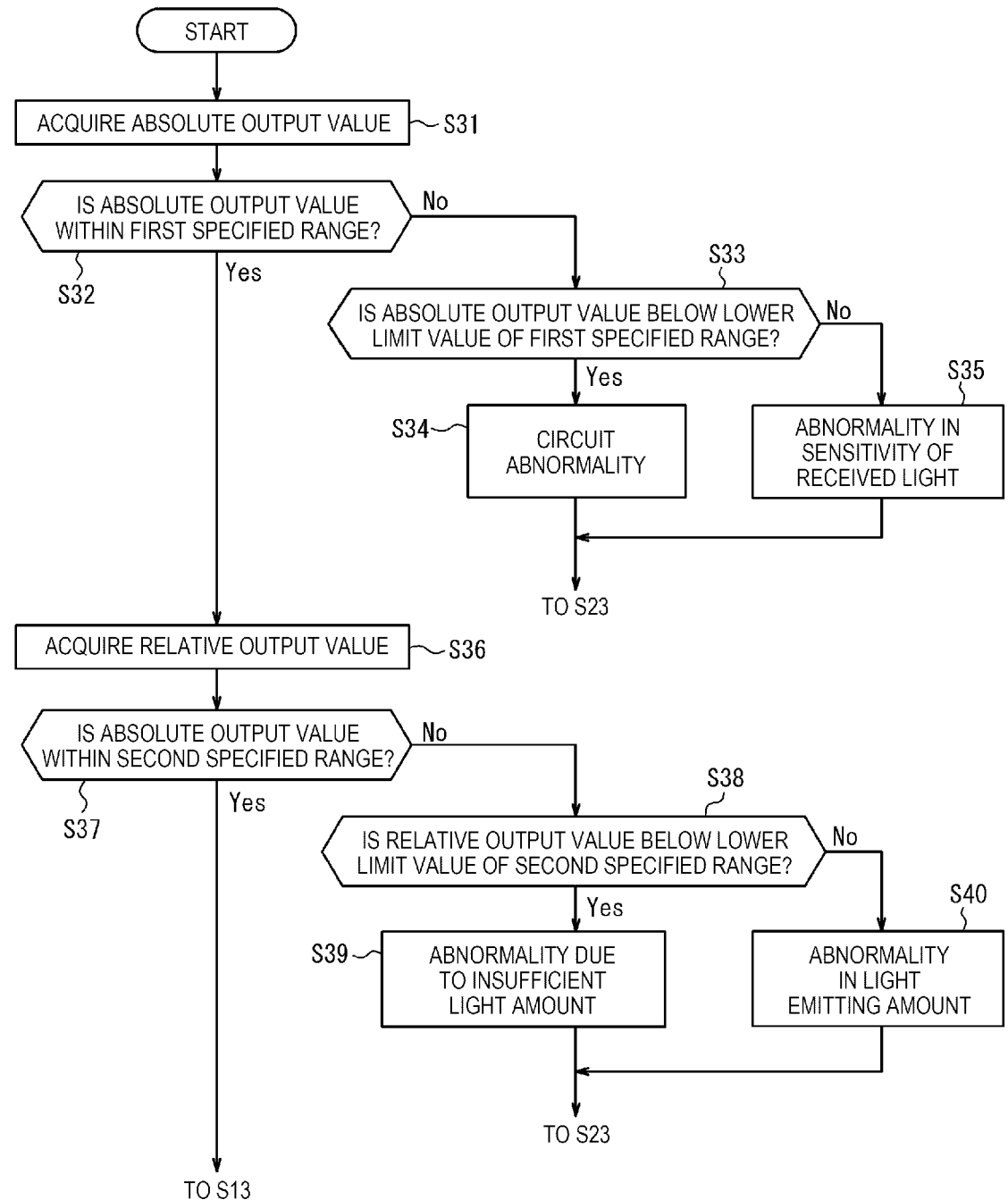

[FIG. 14]
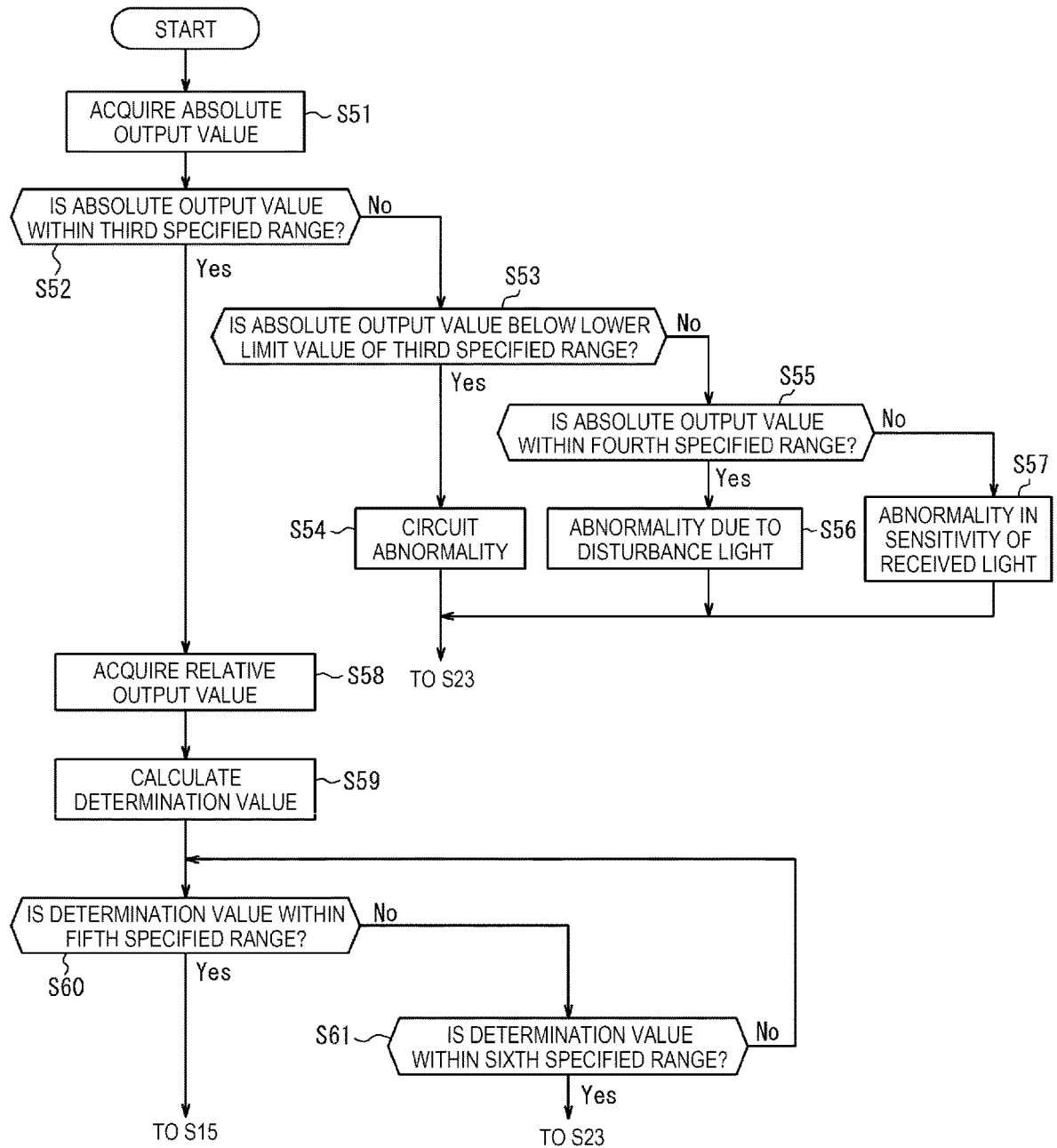

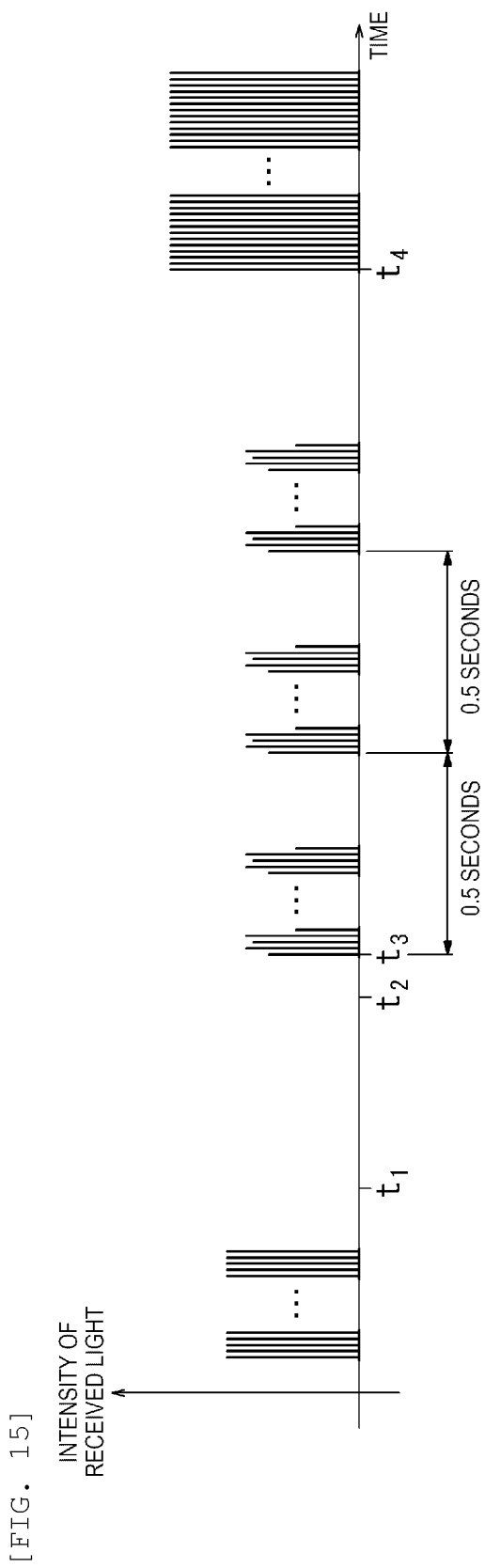
[FIG. 15]

[FIG. 16]
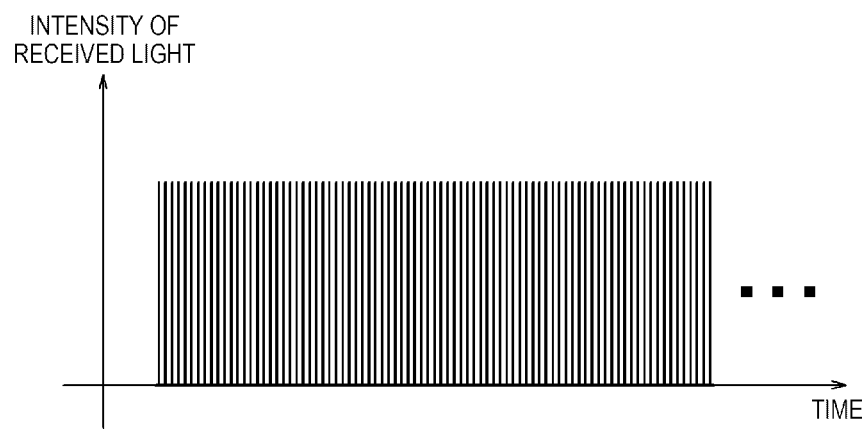

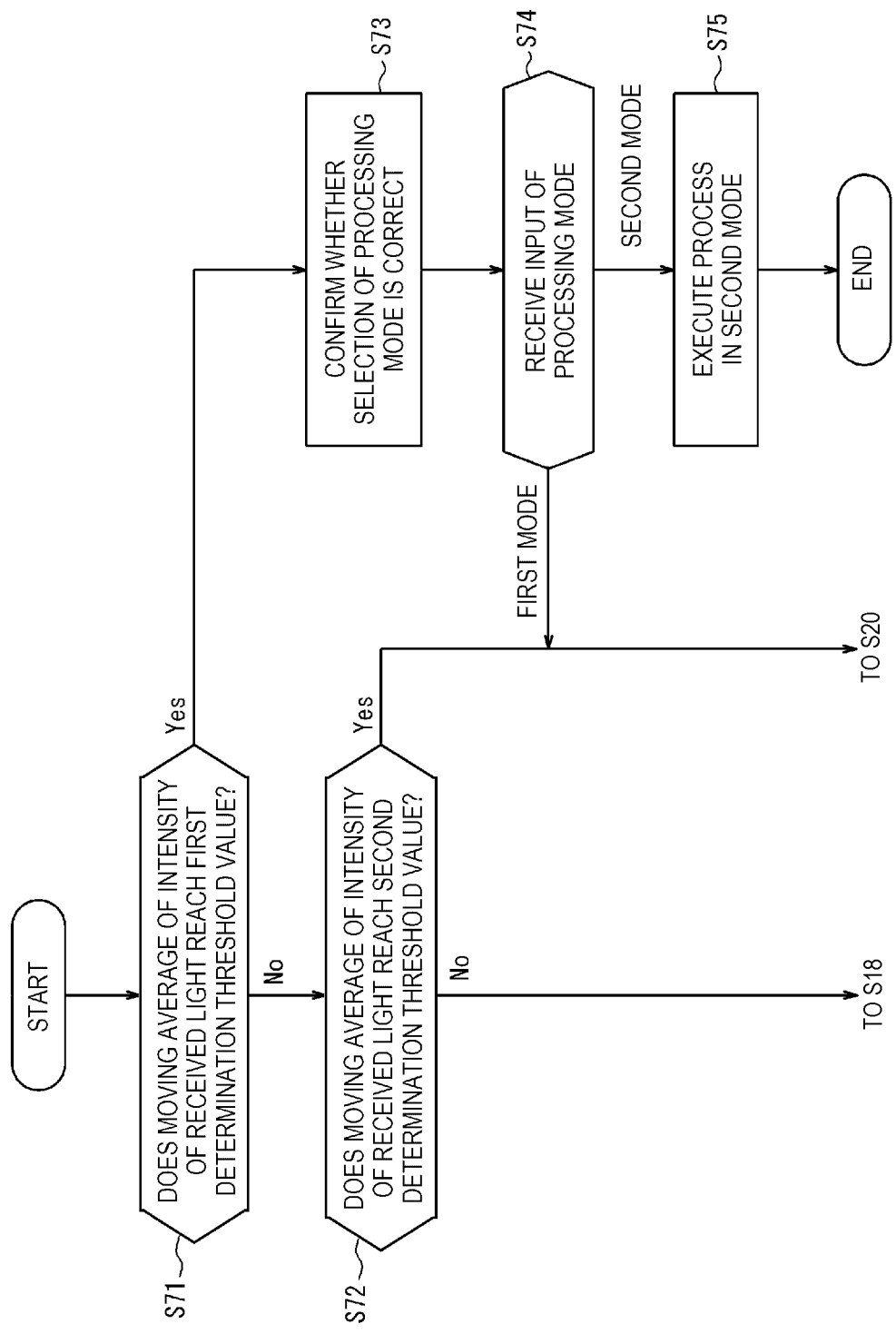
[FIG. 17]

[FIG. 18]

COMPONENT MEASUREMENT APPARATUS, COMPONENT MEASUREMENT APPARATUS SET, AND INFORMATION PROCESSING METHOD

CROSS-REFERENCE TO RELATED APPLICATIONS

This is a bypass continuation of PCT Appl. No. PCT/JP2021/000119, filed on Jan. 5, 2021, which claims priority to Japanese Patent Appl. No. 2020-027564, filed on Feb. 20, 2020. The contents of these applications are hereby incorporated by reference in their entirety.

BACKGROUND

The present disclosure relates to a component measurement apparatus, a component measurement apparatus set, and an information processing method.

In the related art, an apparatus for measuring a component to be measured contained in a sample such as blood as a specimen is known in the biochemistry and medical fields. For example, Japanese Patent Pub. No. 2011-064596-A discloses a blood glucose meter that measures an amount of glucose in blood by applying blood to a measurement chip mounted on the blood glucose meter.

SUMMARY

A device for measuring a component to be measured, such as a blood glucose meter, may be operable in a second mode of confirming the performance of the device in addition to a first mode of measuring the component to be measured. When the device is operated in the first mode, for example, the measurement chip to which the blood is applied is inserted into the device, and when the device is operated in the second mode, a measurement chip to which a solution dedicated for the second mode is applied is inserted into the device to execute the measurement. In this case, an operator of the device inputs an instruction to the device to execute the operation in the first mode or to execute the operation in the second mode. However, the operator may make an erroneous input to the device due to carelessness or the like of the operator. For example, the operator may input a start instruction of the operation in the second mode even though the measurement chip to which the blood is applied is inserted into the device, and conversely, the operator may input a start instruction of the operation in the first mode even though the measurement chip to which the solution dedicated for the second mode is applied is inserted into the device. When the erroneous input is made, the device may not be able to execute an appropriate process.

An object of certain embodiments of the present disclosure is to provide a component measurement apparatus, a component measurement apparatus set, and an information processing method capable of reducing a chance of executing a process based on an erroneous input by an operator.

According to a first aspect of the present disclosure, a component measurement apparatus has a chip insertion space for inserting a component measurement chip provided with a reagent that reacts with a component to be measured in a sample. The component measurement apparatus includes a light emitting unit configured to emit radiation light to the component measurement chip in a state in which the component measurement chip is inserted into the chip insertion space, a light receiving unit configured to receive light transmitted through or reflected from the component measurement chip, and a control unit. The control unit is capable of executing a process in any one of processing modes including a first mode of measuring the component to be measured in the sample and a second mode of confirming performance of the component measurement apparatus using an actual measurement value of an intensity of received light in the light receiving unit. When a difference between a reference intensity of received light in the light receiving unit at a specific time point after the component measurement chip is inserted into the chip insertion space and an intensity of received light received by the light receiving unit exceeds a predetermined value, the control unit determines whether there is a possibility of an incorrect processing mode to be executed.

According to one embodiment of the present disclosure, when a difference between the reference intensity of received light and a moving average value of the intensity of received light received by the light receiving unit exceeds a predetermined value, the control unit determines whether there is a possibility of the incorrect processing mode.

According to one embodiment of the present disclosure, when the control unit determines that there is a possibility of the incorrect processing mode, the control unit outputs to confirm whether the processing mode to be executed is correct.

According to one embodiment of the present disclosure, the control unit determines whether the sample is suitable for use in a processing mode based on whether the difference between the reference intensity of received light and the intensity of received light is higher than the reference intensity of received light by a first determination threshold value or more, or is lower than by the reference intensity of received light a second determination threshold value or more.

According to one embodiment of the present disclosure, when the control unit determines that the sample is not used in the processing mode, the control unit determines that there is a possibility of the incorrect processing mode to be executed.

According to one embodiment of the present disclosure, when the control unit determines that there is a possibility of the incorrect processing mode to be executed, the control unit executes a process in a processing mode other than the processing mode to be executed.

According to one embodiment of the present disclosure, the light emitting unit at least includes: a first light source configured to emit radiation light of a first predetermined wavelength to a mixture of the sample and the reagent in order to determine an amount of the component to be measured; a third light source configured to emit radiation light of a third predetermined wavelength that is used to estimate an amount of noise other than a predetermined coloring component included in an actual measurement value of absorbance of the mixture measured by the radiation light from the first light source, an effect caused by light scattering due to a component contained in the sample being dominant in the radiation light of the third predetermined wavelength; and a fourth light source configured to emit radiation light of a fourth predetermined wavelength that is used to estimate the amount of noise, a ratio of absorbance caused by light absorption due to a predetermined component contained in the sample being equal to or greater than a predetermined value in the radiation light of the fourth predetermined wavelength.

According to one embodiment of the present disclosure, when the first mode is selected as the processing mode to be executed and a difference between the reference intensity of received light and an intensity of received light with respect to the radiation light of the third predetermined wavelength reaches the first determination threshold value, the control unit determines that there is a possibility of an incorrect selection of the processing mode.

According to one embodiment of the present disclosure, when the second mode is selected as the processing mode to be executed and a difference between the reference intensity of received light and an intensity of received light with respect to the radiation light of the fourth predetermined wavelength λ4 reaches the second determination threshold value, the control unit determines that there is a possibility of an incorrect selection of the processing mode.

According to one embodiment of the present disclosure, components derived from the sample are erythrocytes and hemoglobin contained in the erythrocytes.

According to a second aspect of the present disclosure, a component measurement apparatus includes a component measurement chip and a component measurement apparatus having a chip insertion space for inserting the component measurement chip. The component measurement apparatus includes a light emitting unit configured to emit radiation light to the component measurement chip in a state in which the component measurement chip is inserted into the chip insertion space, a light receiving unit configured to at least receive light acquired by the radiation light transmitted through or reflected from the component measurement chip, and a control unit. The control unit is capable of executing a process in any one of processing modes including a first mode of measuring a component to be measured in the sample and a second mode of confirming performance of the component measurement apparatus using an actual measurement value of an intensity of received light in the light receiving unit. When a difference between a reference intensity of received light in the light receiving unit at a specific time point after the component measurement chip is inserted into the chip insertion space and an intensity of received light received by the light receiving unit exceeds a predetermined value, the control unit determines whether there is a possibility of an incorrect selection of the processing mode.

According a third aspect of the present disclosure, an information processing method is executed by a component measurement apparatus having a chip insertion space for inserting a component measurement chip. The component measurement apparatus includes a light emitting unit configured to emit radiation light to the component measurement chip in a state in which the component measurement chip is inserted into the chip insertion space, a light receiving unit configured to receive light acquired by the radiation light transmitted through or reflected from the component measurement chip, and a control unit. The control unit is capable of executing a process in any one of processing modes including a first mode of measuring a component to be measured in the sample and a second mode of confirming performance of the component measurement apparatus using an actual measurement value of an intensity of received light in the light receiving unit. The information processing method includes receiving an input operation of one of the processing modes, and determining, when a difference between a reference intensity of received light in the light receiving unit at a specific time point after the component measurement chip is inserted into the chip insertion space and an intensity of received light received by the light receiving unit exceeds a predetermined value, whether there is a possibility of an incorrect selection of the processing mode.

According to certain embodiments of the present disclosure, it is possible to provide a component measurement apparatus, a component measurement apparatus set, and an information processing method capable of reducing a chance of executing a process based on an erroneous input by an operator.

BRIEF DESCRIPTION OF THE DRAWINGS

FIG. 1 is a top view of a component measurement apparatus set as one embodiment in which a component measurement chip is mounted on a component measurement apparatus.

FIG. 2 is a view illustrating a cross section taken along a line I-I of FIG. 1.

FIG. 3 is a view illustrating a cross section taken along a line II-II of FIG. 1.

FIG. 4 is a top view illustrating the component measurement chip illustrated in FIG. 1.

FIG. 5 is a cross-sectional view along a line III-III of FIG. 4.

FIG. 6 is a functional block diagram of the component measurement apparatus illustrated in FIG. 1.

FIG. 7 is a view illustrating a positional relation among a plurality of light sources in the component measurement apparatus illustrated in FIG. 1.

FIG. 8 is a view illustrating radiation positions, to a mixture, of radiation light emitted by the plurality of light sources illustrated in FIG. 7.

FIG. 9 is a flowchart showing an example of a component measurement process executed by the component measurement apparatus of FIG. 1.

FIG. 10 is a flowchart showing an example of a light amount measurement process executed by the component measurement apparatus of FIG. 1 during the component measurement process.

FIG. 11 is a diagram schematically showing intensities of received light of one set of radiation light emitted from a first light source to a fifth light source of FIG. 7, which are measured by a light receiving unit.

FIG. 12 is a diagram schematically showing intensities of received light of radiation light emitted from the first light source to the fifth light source, which are measured by the light receiving unit.

FIG. 13 is a flowchart showing an example of a determination process of a first intensity of received light.

FIG. 14 is a flowchart showing an example of a determination process of a second intensity of received light.

FIG. 15 is a diagram schematically showing the intensities of received light of the radiation light emitted from the first light source to the fifth light source, which are measured by the light receiving unit.

FIG. 16 is a diagram schematically showing the intensities of received light of the radiation light emitted from the first light source to the fifth light source, which are measured by the light receiving unit.

FIG. 17 is a flowchart showing an example of a determination process of a third intensity of received light.

FIG. 18 is a diagram schematically showing the intensities of received light of the radiation light emitted from the first light source to the fifth light source, which are measured by the light receiving unit.

DETAILED DESCRIPTION

Hereafter, embodiments of a component measurement apparatus, a component measurement apparatus set, and an information processing method according to the present disclosure will be described with reference to FIGS. 1 to 18. In the drawings, common members are denoted by the same reference numerals.

First, a component measurement apparatus according to an embodiment of the present disclosure will be described. FIG. 1 is a top view illustrating a component measurement apparatus set 100 in which a component measurement chip 2 is mounted on a component measurement apparatus 1 according to the present embodiment. FIG. 2 is a cross-sectional view illustrating a cross section taken along a line I-I of FIG. 1, and FIG. 3 is a cross-sectional view illustrating a cross section taken along a line II-II of FIG. 1. FIGS. and 3 illustrate a vicinity of a portion where the component measurement chip 2 is mounted in an enlarged view.

As illustrated in FIGS. 1 to 3, the component measurement apparatus set 100 includes the component measurement apparatus 1 and the component measurement chip 2. The component measurement apparatus 1 according to the present embodiment is a blood glucose level measurement apparatus capable of measuring a concentration of glucose in a blood plasma component as a component to be measured in a sample. The component measurement chip 2 according to the present embodiment is a blood glucose level measurement chip capable of being mounted on one end of the blood glucose level measurement apparatus as the component measurement apparatus 1. The term "sample" here may be whole blood (blood) or may be separated blood plasma. Further, the sample may be an aqueous solution containing glucose.

The component measurement apparatus 1 may be capable of executing a process in a plurality of modes. In the present embodiment, the component measurement apparatus 1 is capable of executing a process in any one of two processing modes that includes a first mode of measuring the component to be measured and a second mode of confirming the performance of the component measurement apparatus 1. The processing mode is selected, for example, by an operator of the component measurement apparatus 1 performing a predetermined input operation to the component measurement apparatus 1. In the present embodiment, the selected processing mode corresponds to a processing mode to be executed. However, when a processing mode is automatically determined by, for example, the component measurement apparatus 1, the determined processing mode becomes the processing mode to be executed.

The component measurement apparatus 1 includes a housing 10 made of a resin material, a button group provided on an upper surface of the housing 10, a display unit 11 that includes, for example, a liquid crystal or a light emitting diode (LED) provided on the upper surface of the housing 10, and a removal lever 12 to be operated when the component measurement chip 2 mounted on the component measurement apparatus 1 is removed. The button group according to the present embodiment includes a power button 13 and an operation button 14.

As illustrated in FIG. 1, the housing 10 includes a main body portion 10a having a substantially rectangular outer shape when viewed from above, on whose upper surface the button group and the display unit 11 are provided, and a chip mounting portion 10b that is projected outward from the main body portion 10a and is provided with the removal lever 12 on an upper surface thereof. As illustrated in FIG. 2, a chip mounting space S having a tip end opening 10s formed on a tip end surface of the chip mounting portion 10b as one end is partitioned inside the chip mounting portion 10b. When the component measurement chip 2 is mounted on the component measurement apparatus 1, the component measurement chip 2 is inserted into the chip mounting space S from the outside through the tip end opening 10s, and the component measurement chip 2 is pushed into a predetermined position. Accordingly, the chip mounting portion 10b of the component measurement apparatus 1 is in a state in which the component measurement chip 2 is locked, so that the component measuring chip 2 can be mounted on the component measurement apparatus 1. The lock of the component measurement chip 2 by the component measurement apparatus 1 can be achieved by various configurations, for example, by providing a claw portion that can engage with a part of the component measurement chip 2 in the chip mounting portion 10b.

When the component measurement chip 2 mounted on the component measurement apparatus 1 is removed from the component measurement apparatus 1, the component measurement chip 2 locked by the chip mounting portion 10b of the component measurement apparatus 1 is unlocked by operating the removal lever 12 from the outside of the housing 10. At the same time, an eject pin 26 (see FIG. 2) in the housing 10 is displaced in conjunction, so that the component measurement chip 2 can be removed from the component measurement apparatus 1.

The housing 10 according to the present embodiment includes the main body portion 10a having a substantially rectangular shape in the top view (see FIG. 1) and the chip mounting portion 10b projected outward from the main body portion 10a. Alternatively, the housing may include a chip mounting portion to which the component measurement chip 2 can be mounted, and is not limited to the shape of the housing 10 according to the present embodiment. Therefore, in addition to the shape of the housing 10 according to the present embodiment, it is possible to adopt various shapes for facilitating gripping by, for example, one hand of an operator.

The display unit 11 can display information on the component to be measured that is measured by the component measurement apparatus 1. In the present embodiment, the concentration of glucose measured by the blood glucose level measurement apparatus as the component measurement apparatus 1 can be displayed on the display unit 11. The display unit 11 may be capable of displaying not only the information on the component to be measured but also various information such as measurement conditions of the component measurement apparatus 1 and instruction information for instructing a predetermined operation to the operator. The operator can operate the power button 13 and the operation button 14 of the button group while checking contents displayed on the display unit 11.

As illustrated in FIGS. 2 and 3, the component measurement apparatus 1 includes a light emitting unit 66 and a light receiving unit 72. As illustrated in FIGS. 2 and 3, in a state in which the component measurement chip 2 is mounted in the chip mounting space S of the component measurement apparatus 1, the component measurement chip 2 is irradiated with radiation light emitted by the light emitting unit 66. The light receiving unit 72 receives transmitted light transmitted through the component measurement chip 2 of the radiation light emitted from the light emitting unit 66 to the component measurement chip 2. In the present embodiment, the light emitting unit 66 and the light receiving unit 72 face each other with the chip mounting space S sandwiched therebetween. The arrangement of the light emitting unit 66 and the light receiving unit 72 is not limited thereto. The light receiving unit 72 may be located at a position where light transmitted through the sample in the component measurement chip 2 can be detected. For example, the light emitting unit 66 and the light receiving unit 72 may be arranged on the same side with respect to the component measurement chip 2, and a reflective member may be provided on a side facing the light emitting unit and the light receiving unit with the chip mounting space S and the sample sandwiched therebetween.

The light emitting unit 66 includes five light sources. Specifically, the light emitting unit 66 includes a first light source 67, a second light source 68a, a third light source 68b, a fourth light source 68c, and a fifth light source 68d. Here, as illustrated in FIG. 2, the first light source 67, the fourth light source 68c, and the fifth light source 68d are arranged at different positions in a flow direction A (a rightward direction in FIG. 2) in which the sample flows in a flow path 23 of the component measurement chip 2 to be described below. As illustrated in FIG. 3, the first light source 67, the second light source 68a, and the third light source 68b are arranged at different positions in a flow path width direction B (both leftward and rightward directions in FIG. 3) orthogonal to the flow direction A. Details of the arrangement of the first light source 67 to the fifth light source 68d will be described below (see FIG. 7).

Next, the component measurement chip 2 will be described. FIG. 4 is a top view illustrating the component measurement chip 2. FIG. 5 is a cross-sectional view along a line III-III of FIG. 4. As illustrated in FIGS. 4 and 5, the component measurement chip 2 includes a base member 21 having a substantially rectangular plate shape, a measurement reagent 22 held by the base member 21, and a cover member 25 covering the base member 21. The cover member 25 may be formed of a member having a light-shielding property at portions other than a portion that is a measurement spot when the component measurement chip 2 is inserted into the component measurement apparatus 1. Details of the measurement spot will be described below.

A groove is defined on a surface of the base member 21 on one side in a thickness direction (in the present embodiment, because the thickness direction is the same direction as a thickness direction C of the component measurement chip 2 illustrated in FIGS. 2 and 3, it is hereinafter referred to as the thickness direction C). The groove of the base member 21 is a hollow portion extending in a direction orthogonal to the thickness direction C by being covered with the cover member 25, and the hollow portion constitutes the flow path 23 of the component measurement chip 2. A supply portion 24 capable of supplying a sample from the outside is formed at one end of the flow path 23. The measurement reagent 22 is held at a groove bottom of the groove of the base member 21 on an inner wall of the flow path 23, and the sample supplied from the outside to the supply portion 24 moves in the flow direction A along the flow path 23 by, for example, capillary phenomenon, reaches a holding position where the measurement reagent 22 is held, and comes into contact with the measurement reagent 22. The measurement reagent 22 contains a coloring reagent that dissolves in the sample and reacts with the component to be measured in the sample to develop a color. Therefore, when the measurement reagent 22 and the component to be measured in the sample come into contact with each other, a color reaction occurs in which the coloring reagent contained in the measurement reagent 22 develops a color, and a coloring component (a reaction product) is generated.

A gap 23a is defined between the cover member 25 and the measurement reagent 22. The sample moving from the supply portion 24 provided at the end to the flow path 23 in the flow direction A dissolves the measurement reagent 22 and reaches the other end of the flow path 23 while reacting. Therefore, by flowing the sample through the entire measurement reagent 22 in the flow direction A, the mixture X containing the coloring component can be spread in a region that may be the measurement spot. Here, the mixture X contains at least the sample, the unreacted or reacted measurement reagent 22, and the coloring component.

For convenience of description, FIG. 2 omits the sample and illustrates the "mixture X" present at the holding position of the measurement reagent 22. Alternatively, the mixture X is diffused not only at the holding position of the measurement reagent 22 but also in the vicinity of the holding position of the measurement reagent 22, for example, at the gap 23a. More specifically, the sample entering the flow path 23 from the supply portion 24 reaches downstream end of the flow path 23 through the gap 23a while being in contact with the measurement reagent 22 at the holding position, and the inside of the flow path 23 is filled with the sample. The measurement reagent 22 is dissolved in the sample, so that the color reaction with the sample proceeds, and the mixture X is located at the holding position and its vicinity.

Although the flow path 23 according to the present embodiment is constituted by the hollow portion partitioned by the base member 21 and the cover member 25, the flow path is not limited to this configuration. The flow path may be constituted by only the groove formed on the outer surface of the base member 21 on one side in the thickness direction C.

As materials of the base member 21 and the cover member 25, it is preferable to use a transparent material and thus an amount of transmitted light after the radiation light is transmitted is a sufficient signal for measurement. For example, transparent organic resin materials such as polyethylene terephthalate (PET), polymethyl methacrylate (PMMA), polystyrene (PS), cyclic polyolefin (COP), cyclic olefin copolymer (COC), and polycarbonate (PC); and transparent inorganic materials such as glass and quartz can be used.

The measurement reagent 22 contains a coloring reagent that reacts with the component to be measured in the sample to cause a color reaction that develops a color according to a blood concentration of the component to be measured. The measurement reagent 22 according to the present embodiment is applied to the groove bottom of the groove as the flow path 23. The measurement reagent 22 according to the present embodiment reacts with glucose as the component to be measured in the sample. Examples of the measurement reagent 22 according to the present embodiment include, for example, a mixed reagent of (i) glucose oxidase (GOD), (ii) peroxidase (POD), (iii) 1-(4-sulfophenyl)-2,3-dimethyl-4-amino-5-pyrazolone, (iv) N-ethyl-N-(2-hydroxy-3-sulfopropyl)-3,5-dimethylaniline, sodium salt, and monohydrate (MAOS), or a mixed reagent of glucose dehydrogenase (GDH) and tetrazolium salt.

Further, the measurement reagent may contain a buffer such as a phosphate buffer, and a mediator. The kinds and components of the measurement reagent 22 are not limited to these.

However, in the measurement reagent 22 according to the present embodiment, a coloring reagent is selected whose peak wavelength in an absorbance spectrum of a coloring component generated by a color reaction with glucose in the sample is different from a peak wavelength due to light absorption characteristics of hemoglobin in blood cells. The coloring reagent contained in the measurement reagent 22 according to the present embodiment has a peak wavelength around 660 nm of the absorbance spectrum of the coloring component. However, the coloring reagent is not limited to a coloring reagent whose peak wavelength is around 660 nm, and is appropriately selected according to the purpose.

As illustrated in FIG. 2, when the component to be measured is measured by the component measurement apparatus 1, the component measurement chip 2 is mounted on the chip mounting portion 10b. When the sample is supplied to the supply portion 24 provided at one end of the component measurement chip 2, the sample moves in the flow path 23 due to, for example, the capillary phenomenon, reaches the holding position of the flow path 23 where the measurement reagent 22 is held, and then glucose in the sample (the blood plasma) reacts with the measurement reagent 22 at the holding position. Further, at the holding position of the flow path 23, the mixture X containing a coloring component is generated. The so-called colorimetric component measurement apparatus 1 irradiates the mixture X containing a coloring component with the radiation light, detects the amount of transmitted light (or the amount of reflected light), and obtains a detection signal that correlates with the intensity of color development according to the blood concentration. Further, the component measurement apparatus 1 can measure the component to be measured by referring to a calibration curve created in advance. As described above, the component measurement apparatus 1 according to the present embodiment can measure the concentration of glucose in the blood plasma component in the sample.

FIG. 6 is a functional block diagram of the component measurement apparatus 1 illustrated in FIGS. 1 to 3. As illustrated in FIG. 6, the component measurement apparatus 1 includes a control unit 50, a light measurement unit 51, a storage unit 52, a temperature measurement unit 53, a power supply unit 54, a battery 55, a communication unit 56, a clock unit 57, an operation unit 58, a buzzer unit 59, and the display unit 11.

The control unit 50 is implemented by a micro-processing unit (MPU) or a central processing unit (CPU), and can implement a control operation of each unit by reading and executing a program stored in the storage unit 52 or the like. The storage unit 52 is implemented by a non-transitory storage medium that is volatile or non-volatile, and can read or write various kinds of data (including a program) necessary for executing a component measurement method illustrated in the present embodiment.

When the control unit 50 operates in the first mode, the control unit 50 can measure the component to be measured in the sample by operating the light measurement unit 51. Further, the control unit 50 can execute a process of detecting whether a normal measurement can be executed when the component measurement apparatus 1 executes the measurement process of the component to be measured. The control unit 50 can further execute a process of determining whether there is a possibility of an incorrect selection of the processing mode. Details of the process of measuring the component to be measured, the process of detecting whether the normal measurement can be executed, and the process of determining whether there is a possibility of an incorrect selection of the processing mode will be described below.

The light measurement unit 51 is an optical system capable of acquiring optical characteristics of the mixture X containing the sample and the coloring component. Specifically, the light measurement unit 51 includes the light emitting unit 66, and the light receiving unit 72.

The light emitting unit 66 emits radiation light toward the chip insertion space S. The light emitting unit 66 includes a plurality of light sources. Specifically, the light emitting unit 66 according to the present embodiment includes five light sources that emit radiation light (for example, visible light and infrared light) having different spectral radiation characteristics. More specifically, as described above, the light emitting unit 66 according to the present embodiment includes the first light source 67, the second light source 68a, the third light source 68b, the fourth light source 68c, and the fifth light source 68d. Positional relations among the first light source 67 to the fifth light source 68d are positional relations illustrated in FIGS. 2 and 3. Details of actual positional relations among the first light source 67 to the fifth light source 68d will be described below (see FIG. 7).

Peak wavelengths of light emitted from the first light source 67 to the fifth light source 68d are λ1 to λ5, respectively. As the first light source 67 to the fifth light source 68d, various light emitting elements such as a LED element, an organic electro-luminescence (EL) element, an inorganic EL element, and a laser diode (LD) element can be applied. As the first light source 67 to the fifth light source 68d, the above described LED element is easily used in consideration of versatility and the like. In the present embodiment, the first light source 67 to the fifth light source 68d are implemented by LED elements. Hereinafter, the above described "peak wavelength" will be described as the wavelength of light emitted from each light source. For convenience of description, the peak wavelength λ1 of the first light source 67 is referred to as the "first predetermined wavelength λ1", the peak wavelength λ2 of the second light source 68a is referred to as the "second predetermined wavelength λ2", the peak wavelength λ3 of the third light source 68b is referred to as the "third predetermined wavelength λ3", the peak wavelength λ4 of the fourth light source 68c is referred to as the "fourth predetermined wavelength λ4", and the peak wavelength λ5 of the fifth light source 68d is referred to as the "fifth predetermined wavelength λ5". The "peak wavelength" in the present embodiment is shown by one numerical value for convenience, and may also include a wavelength range within ±20 nm of each numerical value.

The light receiving unit 72 receives transmitted light or reflected light of the radiation light emitted from the light emitting unit 66, which is in a region where the coloring component is located. As illustrated in FIGS. 2 and 3, the light receiving unit 72 according to the present embodiment is implemented by one light receiving element that faces the light emitting unit 66 with the component measurement chip 2 sandwiched therebetween. In the present embodiment, the light receiving unit 72 receives the transmitted light that is applied from the first light source 67 to the fifth light source 68d of the light emitting unit 66 to the mixture X generated at the holding position of the component measurement chip 2 for the measurement reagent 22 and transmits through the component measurement chip 2. As the light receiving unit 72, various photoelectric conversion elements including a photo diode (PD) element, a photoconductor, and a photo transistor (PT) can be applied.

In the present description, hereinafter, among regions irradiated with the radiation light from the light emitting unit 66 in the component measurement apparatus 1, a region irradiated with the radiation light that can be detected by the light receiving unit 72 is referred to as a measurement region. When the measurement is executed, there is the coloring component (or the mixture X) to be detected in the measurement region.

Each of the first light source 67 to the fifth light source 68d receives a drive power signal from a light emission control circuit included in the light measurement unit 51, and turns on and off based on the drive power signal. The light receiving unit 72 outputs an analog signal corresponding to the received light. The analog signal undergoes amplification and AD conversion, and is converted into a digital signal (hereinafter referred to as a detection signal) by a light receiving control circuit included in the light measurement unit 51.

Referring to FIG. 6 again, the storage unit 52 can be implemented by a semiconductor memory, a magnetic memory, or the like. The storage unit 52 stores, for example, various types of information and a program for operating the component measurement apparatus 1. The storage unit 52 may also function as a work memory.

The temperature measurement unit 53 measures a temperature in the vicinity of the component measurement chip 2. The temperature measurement unit 53 measures, for example, a temperature in the chip mounting space S. The temperature measurement unit 53 may be implemented by, for example, a known thermometer. The temperature measured by the temperature measurement unit 53 can be used, for example, in adjusting the amount of radiation light emitted from the light emitting unit 66, which will be described below.

The power supply unit 54 supplies electric power stored in the battery 55 to each functional unit of the component measurement apparatus 1.

The communication unit 56 transmits and receives various types of information by performing wired communication or wireless communication with an external device. For example, the communication unit 56 transmits a result of the component measurement by the component measurement apparatus 1 to an external device connected communicably. The communication unit 56 may receive a signal for executing an operation by the component measurement apparatus 1 from the external device connected communicably.

The clock unit 57 measures time and ticks the time. The clock unit 57 may be implemented by, for example, a real time clock (RTC).

The operation unit 58 is an input interface for the operator of the component measurement apparatus 1 to perform an input operation on the component measurement apparatus 1. In the present embodiment, the operation unit 58 includes the power button 13 and the operation button 14. However, the configuration of the operation unit 58 is not limited to the power button 13 and the operation button 14, and may be achieved in any aspect by which the operator can perform an input operation. The operator can select (determine) whether to execute, with the component measurement apparatus 1, the first mode or the second mode, for example, by operating the operation unit 58.

The buzzer unit 59 reports information by outputting a buzzer sound. The buzzer unit 59 outputs the buzzer sound at a predetermined timing set in advance. For example, the buzzer unit 59 outputs the buzzer sound when a process of the component measurement by the component measurement apparatus 1 is completed, or when a problem occurs in the component measurement apparatus 1.

Next, the measurement process of the component to be measured in the sample executed by the control unit 50 of the component measurement apparatus 1 in the first mode, and the arrangement of the first light source 67 to the fifth light source 68$d$ will be described.

The control unit 50 instructs a measurement operation to the light measurement unit 51, and measures the concentration of the component to be measured using the detection signal acquired by the light measurement unit 51 and various kinds of data.

The storage unit 52 stores actual measurement value data including a first actual measurement value D1 to a fifth actual measurement value D5, which are the absorbance of the mixture X at each of the first predetermined wavelength $\lambda 1$ to the fifth predetermined wavelength $\lambda 5$ measured by the light measurement unit 51, correction coefficient data including a group of correction coefficients that correlate with the absorbance of the mixture X at each of the second predetermined wavelength $\lambda 2$ to the fifth predetermined wavelength $\lambda 5$, and calibration curve data such as a calibration curve showing a relation between the absorbance of the coloring component in the mixture X, which is acquired by correcting the absorbance of the mixture X measured at the first predetermined wavelength $\lambda 1$ with the correction coefficient data, and various physical quantities (for example, the concentration of glucose), and a calibration curve showing a relation between the absorbance of hemoglobin in the mixture X and a hematocrit value. The term "hematocrit value" is a value indicating a volume ratio of blood cell components in blood as a sample to the blood (the whole blood) by a percentage.

The component measurement apparatus 1 can measure the component to be measured in the sample based on the optical characteristics of the mixture X containing the coloring component generated by the color reaction between the component to be measured in the sample and the reagent. Specifically, the component measurement apparatus 1 can estimate an amount of noise other than the coloring component included in the first actual measurement value D1 of absorbance of the mixture X measured by irradiating the mixture X with the radiation light of the first predetermined wavelength $\lambda 1$ as a measurement wavelength, using the radiation light of the second predetermined wavelength $\lambda 2$ to the fifth predetermined wavelength $\lambda 5$. More specifically, the component measurement apparatus 1 can estimate the amount of noise using the second actual measurement value D2 to the fifth actual measurement value D5 of the absorbance of the mixture X measured by irradiating the mixture X with the radiation light of the second predetermined wavelength $\lambda 2$ to the fifth predetermined wavelength $\lambda 5$, and can measure the absorbance of the coloring component and further the component to be measured.

FIG. 7 is a view showing the positional relations among the first light source 67 to the fifth light source 68$d$ when viewed from the upper surface (see FIG. 1) side of the component measurement apparatus 1. In FIG. 7, for convenience of description, a position of the light receiving unit 72 in the flow path 23 of the component measurement chip 2 is shown by a two-dot chain line, and in the present embodiment, the mixture X is generated at or near the holding position in the flow path 23.

As illustrated in FIGS. 2, 3 and 7, the first light source 67 to the fifth light source 68$d$ face the mixture X located in the flow path 23 for the sample. More specifically, the first light source 67 to the fifth light source 68$d$ according to the present embodiment face the holding position of the measurement reagent 22 in the flow path 23 for the sample in a direction orthogonal to both the flow direction A and the flow path width direction B (the same direction as the thickness direction C of the component measurement chip 2 in the present embodiment).

As illustrated in FIGS. 3 and 7, the first light source 67 and the second light source 68$a$ are arranged side by side along the flow path width direction B orthogonal to the flow direction A of the sample at the position of the mixture X in the flow path 23 for the sample. In the present embodiment, the first light source 67 and the second light source 68a are arranged such that a first radiation position SL1 on the mixture X of the radiation light from the first light source 67 and a second radiation position SL2 on the mixture X of the radiation light from the second light source 68a overlap in the flow path width direction B.

Further, as illustrated in FIGS. 3 and 7, the first light source 67, the second light source 68a, and the third light source 68b are arranged side by side along the flow path width direction B with the first light source 67 as a center. In the present embodiment, as illustrated in FIG. 8, the first light source 67 and the third light source 68b are arranged such that a region of the first radiation position SL1 on the mixture X of the radiation light from the first light source 67 in the flow direction A and a region of a third radiation position SL3 on the mixture X of the radiation light from the third light source 68b in the flow direction A overlap in the flow path width direction B.

That is, the first light source 67 to the third light source 68b are arranged such that respective radiation positions thereof overlap in the flow path width direction B. It is preferable that the first light source 67 to the third light source 68b are arranged side by side along the flow path width direction B, and regions of the first radiation position SL1 to the third radiation position SL3 in the flow direction A overlap in the flow path width direction B. Further, it is more preferable that the first light source 67 to the third light source 68b are arranged such that regions of the first radiation position SL1 to the third radiation position SL3 in the flow path width direction B overlap in the flow direction A as well.

In the present embodiment, the first light source 67 and the second light source 68a are arranged adjacent to each other in the flow path width direction B, and there is no gap between the first light source 67 and the second light source 68a where another light source can be arranged. Further, the first light source 67 and the third light source 68b are arranged adjacent to each other in the flow path width direction B, and there is also no gap between the first light source 67 and the third light source 68b where another light source can be arranged. In this way, the first light source 67, the second light source 68a, and the third light source 68b are arranged adjacently in the flow path width direction B without interposing another light source therebetween.

As illustrated in FIGS. 2 and 7, the first light source 67 and the fourth light source 68c are arranged side by side along the flow direction A. Further, as illustrated in FIGS. 2 and 7, the first light source 67 and the fifth light source 68d according to the present embodiment are arranged side by side along the flow direction A. That is, the first light source 67, the fourth light source 68c, and the fifth light source 68d are arranged side by side along the flow direction A with the first light source 67 as a center.

In the present embodiment, the first light source 67 and the fourth light source 68c are arranged side by side along the flow direction A such that the first radiation position SL1 on the mixture X of the radiation light from the first light source 67 and a fourth radiation position SL4 on the mixture X of the radiation light from the fourth light source 68c have an overlapping region after setting a difference in an incidence angle to the mixture X to a predetermined value or less. More specifically, there is no gap between the first light source 67 and the fourth light source 68c in the flow direction A where another light source can be arranged, and the first light source 67 and the fourth light source 68c are adjacent to each other in the flow direction A.

The first light source 67 and the fifth light source 68d are also arranged side by side along the flow direction A such that the first radiation position SL1 on the mixture X of the radiation light from the first light source 67 and a fifth radiation position SL5 on the mixture X of the radiation light from the fifth light source 68d can have an overlapping region after setting the difference in the incidence angle to the mixture X to the predetermined value or less. More specifically, there is no gap between the first light source 67 and the fifth light source 68d in the flow direction A where another light source can be arranged, and the first light source 67 and the fifth light source 68d are adjacent to each other in the flow direction A.

As illustrated in FIG. 7, the first light source 67 to the fifth light source 68d according to the present embodiment are held by a thin plate-like holder member 80. The holder member 80 according to the present embodiment has a cross-shaped outer shape in a top view, and the first light source 67 is held at a central portion (an intersection portion of the cross) in the top view. The second light source 68a is held at a position on one side of the central portion where the first light source 67 is held in the flow path width direction B, and the third light source 68b is held at a position on the other side in the flow path width direction B. Further, the fifth light source 68d is held at a position to the central portion where the first light source 67 is held in the flow direction A, and the fourth light source 68c is held at an opposite position in the flow direction A.

Here, in the present embodiment, the second light source 68a and the third light source 68b that emit the radiation light of the second predetermined wavelength $\lambda 2$ and the radiation light of the third predetermined wavelength $\lambda 3$ are arranged side by side along the flow path width direction B with respect to the first light source 67. Further, the fourth light source 68c and the fifth light source 68d that emit the radiation light of the fourth predetermined wavelength $\lambda 4$ and the radiation light of the fifth predetermined wavelength $\lambda 5$ are arranged side by side along the flow direction A with respect to the first light source 67. Although details will be described below, the second predetermined wavelength $\lambda 2$ and the third predetermined wavelength $\lambda 3$ are wavelengths in an infrared region, and the fourth predetermined wavelength $\lambda 4$ and the fifth predetermined wavelength $\lambda 5$ are wavelengths in a visible region.

In the present embodiment, as illustrated in FIGS. 2 and 3, the light receiving unit 72 faces the first light source 67 to the fifth light source 68d in the thickness direction C with the mixture X located in the flow path 23 of the mounted component measurement chip 2 sandwiched therebetween, and receives the transmitted light acquired by the radiation light from the first light source 67 to the fifth light source 68d transmitted through the mixture X. As illustrated in FIGS. 2 and 3, the component measurement apparatus 1 includes a first aperture portion 69a that is located between the mixture X and the light receiving unit 72 and adjusts the amount of light reaching the light receiving unit 72 of the transmitted light transmitted through the mixture X. A difference between an incidence angle of the radiation light from the first light source 67 to the mixture X and an incidence angle of the radiation light from each of the second light source 68a to the fifth light source 68d to the mixture X affects estimation accuracy of the amount of noise. Therefore, the smaller the difference between the incidence angle of the radiation light from the first light source 67 to the mixture X and the incidence angle of the radiation light from each of the second light source 68a to the fifth light source 68d to the mixture X is, the more preferable. That is, it is preferable to lengthen a distance T1 between the first light source 67 to the fifth light source 68d and the first aperture portion 69a in an opposing direction (in FIGS. 2 and 3, the same direction as the thickness direction C of the component measurement chip 2) in order to improve the estimation accuracy of the amount of noise. On the other hand, by reducing a distance T2 between the first light source 67 to the fifth light source 68d and the light receiving unit 72 in the opposing direction, it is possible to improve light efficiency and to reduce the size of the component measurement apparatus 1.

When a deviation (hereinafter, referred to as "measurement visual field difference") between the region of the first radiation position SL1 of the first light source 67 and each of the regions of the second radiation position SL2 to the fifth radiation position SL5 of the second light source 68a to the fifth light source 68d is large, measurement portions do not coincide with each other, and thus an accuracy of a measurement result of the component to be measured may decrease. Thus, it is preferable to reduce the measurement visual field difference. Therefore, it is preferable to shorten a distance T3 between the mixture X and the first aperture portion 69a in the opposing direction (in FIGS. 2 and 3, the same direction as the thickness direction C of the component measurement chip 2). More preferably, in addition to the first aperture portion 69a, one surface of the component measurement chip 2 is formed of a light-shielding member and an opening through which measurement light can transmit is provided to form an aperture. In this case, only the measurement spot may be formed of a transparent member to form the aperture, or the light-shielding member may be cut out to form the aperture.

Further, as illustrated in FIGS. 2 and 3, the component measurement apparatus 1 includes a second aperture portion 69b that is located between the first light source 67 to the fifth light source 68d and the mixture X and adjusts the amount of light reaching the mixture X from the first light source 67 to the fifth light source 68d. In particular, the second aperture portion 69b is preferably designed such that light reflected by an inner wall of the second aperture portion 69b (hereinafter, referred to as "stray light") of the light emitted from the first light source 67 to the fifth light source 68d does not enter the first aperture portion 69a. The light emitted from the first light source 67 to the fifth light source 68d can be considered to be attenuated to 5% by one wall surface reflection and disappear by three or more multiple reflections. Therefore, in the present embodiment, if the stray light reflected by the inner wall of the second aperture portion 69b does not reach the first aperture portion 69a and is reflected by a certain wall surface, the stray light does not enter the first aperture portion 69a due to the multiple reflection. In the present embodiment, an optical axis of each light source is designed to be mirror-reflected by the inner wall of the second aperture portion 69b. However, actually, the optical axis is diffusely reflected by the inner wall of the second aperture portion 69b, and there is a predetermined distribution in the stray light. Therefore, in the present embodiment, it is preferable to set a distance T4 or the like such that even when a part of the stray light enters the first aperture portion 69a, the incidence angle of the stray light has a difference equal to or smaller than a predetermined value from the incidence angle of the first light source 67.

The component measurement chip 2 that partitions the flow path 23 through which the sample flows and is provided with the measurement reagent 22 containing a coloring reagent in the flow path 23 can be mounted on the component measurement apparatus 1 according to the present embodiment. The coloring reagent causes a color reaction with the component to be measured in the sample. The component measurement apparatus 1 according to the present embodiment is provided with the component measurement chip 2, and can measure the component to be measured in the sample based on the optical characteristics of the mixture containing the coloring component generated by the reaction with the component to be measured in the flow path 23. The component measurement apparatus 1 preferably has a configuration in which the disposable component measurement chip 2 can be attached and detached.

Next, a method for calculating the concentration of the component to be measured in the sample in the first mode by the control unit 50 of the component measurement apparatus 1 according to the present embodiment will be described.

In the present embodiment, the component measurement apparatus 1 performs the color reaction between the sample (for example, the whole blood) and the coloring reagent without separating the blood plasma component containing glucose from the sample by the color reaction between glucose as the component to be measured in the sample and the coloring reagent in the measurement reagent 22. The component measurement apparatus 1 can estimate the absorbance at a predetermined measurement wavelength of the coloring component generated by the color reaction between glucose and the coloring reagent based on the absorbance of the entire mixture X acquired by the color reaction at various wavelengths, and can calculate the concentration of the component to be measured.

Generally, when a sample contains a component to be measured other than a coloring component, an effect as a disturbance factor (noise) may be added to a measurement result of a concentration of the component to be measured based on the absorbance of the coloring component due to the optical phenomenon. For example, when "light scattering" due to the blood cell components in the sample, a surface of the component measurement chip, or fine particles such as dust adhering to the component measurement chip, or the like, or "light absorption" due to a pigment component (specifically, mainly hemoglobin when the sample is the blood) different from the coloring component to be measured occurs, an absorbance higher than a true value tends to be measured.

When the absorbance resulting from the coloring component is accurately measured using the mixture X containing a sample having specific absorption characteristics in addition to the coloring component to be measured, it is necessary to remove the disturbance factor (the noise) caused by the sample-derived absorption characteristics from the actual measurement value of the absorbance at the predetermined measurement wavelength.

The disturbance factor when the sample is the blood may include the light scattering due to the blood cell components, the light absorption due to hemoglobin, and the like. More specifically, it is necessary to estimate an amount of the disturbance factor (the noise) such as the light scattering due to the blood cell components or the light absorption due to hemoglobin at a predetermined measurement wavelength (for example, 660 nm) in which a light absorption rate of the coloring component to be measured is high, and to correct the actual measurement value of the absorbance at the same measurement wavelength. The component measurement apparatus 1 according to the present embodiment performs the correction and calculates the concentration of the component to be measured.

In the present embodiment, the component measurement apparatus 1 can measure the component to be measured in the sample based on the optical characteristics of the mixture X containing the coloring component generated by the color reaction between the sample and the measurement reagent 22. Specifically, in the present embodiment, the concentration of glucose contained in the blood plasma component in the sample is measured.

Here, a measurement principle for the concentration of glucose and the wavelengths $\lambda 1$ to $\lambda 5$ of the radiation light emitted by the first light source 67 to the fifth light source 68d, respectively, will be described. Hemoglobin in erythrocytes mainly contains oxygenated hemoglobin bound to oxygen and reduced hemoglobin in which oxygen is dissociated in a place where an oxygen partial pressure is small. The reduced hemoglobin passes through lungs, and binds to oxygen, and the oxygenated hemoglobin carries oxygen through arteries throughout a body, and the oxygenated hemoglobin can be abundantly found in arterial blood. For example, when blood as a sample is collected from a finger pad, the amount of the oxygenated hemoglobin is relatively large because the blood is blood in capillaries. On the contrary, the reduced hemoglobin can be abundantly found in venous blood.

As an existing technique, it is common practice to use, for example, a hematocrit value to correct absorbance, which is acquired at a measurement wavelength corresponding to a coloring component to be measured, without considering a ratio of the reduced hemoglobin to the oxygenated hemoglobin. However, an absorption coefficient of the reduced hemoglobin and an absorption coefficient of the oxygenated hemoglobin do not coincide with each other, and an absorption amount by the reduced hemoglobin and an absorption amount by the oxygenated hemoglobin differ depending on the wavelength. For example, when the measurement wavelength for measuring the absorbance of the coloring component to be measured is 660 nm, the absorption coefficient of the reduced hemoglobin is about 0.9 and the absorption coefficient of the oxygenated hemoglobin is about 0.09. That is, when the ratio of the oxygenated hemoglobin to the reduced hemoglobin is 1:1, the absorption coefficient of the oxygenated hemoglobin corresponds to about 10% of an absorption coefficient of total hemoglobin. In order to more accurately estimate the absorbance resulting from the coloring component to be measured, it is important to consider the ratio of the reduced hemoglobin to the oxygenated hemoglobin.

Therefore, in the component measurement apparatus 1, the measurement wavelength (the first predetermined wavelength $\lambda 1$) for measuring the absorbance of the coloring component contained in the mixture X is set to 660 nm, and correction is performed to remove the effect of the light scattering due to the blood cell components or the like or the effect of the light absorption due to hemoglobin in consideration of the ratio of the reduced hemoglobin to the oxygenated hemoglobin as the disturbance factor (the noise) from the actual measurement value of the absorbance of the mixture X measured at the measurement wavelength. Accordingly, the absorbance of the coloring component contained in the mixture X is estimated, and the concentration of glucose is calculated using a calibration curve showing a relation between the estimated absorbance and the concentration of glucose.

Hereinafter, further details of the component measurement method executed by the component measurement apparatus 1 will be described.

First, the coloring reagent in the measurement reagent 22 used in the present embodiment has a peak in the absorbance of the coloring component generated by the color reaction with glucose in the sample at around 600 nm. However, in the present embodiment, the measurement wavelength for measuring the absorbance of the coloring component is 660 nm.

The measurement wavelength for measuring the absorbance of the coloring component to be measured may use a wavelength at which the light absorption rate of the coloring component is relatively large and the effect of the light absorption due to hemoglobin is relatively small. Specifically, the measurement wavelength may use a wavelength belonging to a wavelength range W3 that corresponds to a full width region at half maximum of a peak wavelength region in the absorbance spectrum of the coloring component to be measured and has a relatively small ratio of the absorbance caused by the light absorption due to hemoglobin to a total absorbance. A wavelength range corresponding to "a full width region at half maximum of a peak wavelength region" indicates a range from a wavelength showing a half maximum on a short wavelength side to a wavelength showing a half maximum on a long wavelength side when the full width region at half maximum of the peak wavelength region in the absorbance spectrum is specified. The absorbance spectrum of the coloring component to be measured in the present embodiment has a peak wavelength at around 600 nm and a wavelength range of about 500 nm to about 700 nm corresponding to the full width region at half maximum. Further, the effect caused by the light absorption due to hemoglobin in the total absorbance is relatively small in a wavelength range of 600 nm or more. Therefore, in the present embodiment, the wavelength range W3, which corresponds to the full width region at half maximum of the peak wavelength region in the absorbance spectrum of the coloring component to be measured and has the relatively small ratio of the absorbance caused by the light absorption due to hemoglobin to the total absorbance, is 600 nm or more and 700 nm or less. Thus, the measurement wavelength is not limited to 660 nm in the present embodiment, and another wavelength belonging to the range of 600 nm to 700 nm may be used as the measurement wavelength. The absorbance of the coloring component can be measured more accurately at a wavelength in a wavelength range in which a signal indicating the absorbance of the coloring component is strong and the ratio of the absorbance caused by the light absorption due to hemoglobin to the total absorbance is reduced as much as possible, and thus it is preferable that the measurement wavelength is a wavelength at around 660 nm, which is a slightly longer wavelength than the wavelength at around 600 nm that is the peak wavelength in the absorbance spectrum of the coloring component. More specifically, the measurement wavelength is preferably a wavelength belonging to a range of 630 nm to 680 nm, more preferably a wavelength belonging to a range of 640 nm to 670 nm, and particularly preferably a wavelength at 660 nm as in the present embodiment. A tetrazolium salt is preferable as an example of such a coloring reagent.

Further, in the present embodiment, although a coloring reagent is used in which the full width region at half maximum of the peak wavelength region in the absorbance spectrum of the coloring component is about 500 nm to about 700 nm, a coloring reagent may be used in which the full width region at half maximum of the peak wavelength region is different from this range. However, as described above, it is desirable that the wavelength range (600 nm or less) at which the absorbance caused by the light absorption due to hemoglobin increases and the measurement wavelength in the absorbance spectrum of the coloring component do not overlap in consideration of the absorption characteristics of hemoglobin.

Hereinafter, a method for estimating the absorbance of the coloring component at the measurement wavelength of 660 nm of the present embodiment will be described. The component measurement apparatus 1 actually measures the absorbance of the mixture X at each of the four wavelengths including the second predetermined wavelength $\lambda 2$ to the fifth predetermined wavelength $\lambda 5$ that are different from the measurement wavelength (660 nm), corrects the first actual measurement value D1 of the absorbance of the mixture X at the measurement wavelength using four actual measurement values including the second actual measurement value D2 to the fifth actual measurement value D5 and predetermined correction coefficient data, and estimates the absorbance of the coloring component at the measurement wavelength. The measurement wavelength according to the present embodiment is the first predetermined wavelength $\lambda 1$.

As the four actual measurement values including the second actual measurement value D2 to the fifth actual measurement value D5, the component measurement apparatus 1 uses two actual measurement values including the second actual measurement value D2 and the third actual measurement value D3 of the absorbance of the mixture X at two predetermined wavelengths including the second predetermined wavelength $\lambda 2$ and the third predetermined wavelength $\lambda 3$ on a longer wavelength side than the first predetermined wavelength $\lambda 1$ that is the measurement wavelength, and two actual measurement values including the fourth actual measurement value D4 and the fifth actual measurement value D5 of the absorbance of the mixture X at two predetermined wavelengths including the fourth predetermined wavelength $\lambda 4$ and the fifth predetermined wavelength $\lambda 5$ on a shorter wavelength side than the first predetermined wavelength $\lambda 1$ that is the measurement wavelength.

More specifically, as the four actual measurement values including the second actual measurement value D2 to the fifth actual measurement value D5, the component measurement apparatus 1 uses two actual measurement values of the absorbance of the mixture X including the second actual measurement value D2 and the third actual measurement value D3 at two predetermined wavelengths including the second predetermined wavelength $\lambda 2$ and the third predetermined wavelength $\lambda 3$, and two actual measurement values of the absorbance of the mixture X including the fourth actual measurement value D4 and the fifth actual measurement value D5 at two predetermined wavelengths including the fourth predetermined wavelength $\lambda 4$ and the fifth predetermined wavelength $\lambda 5$. The second predetermined wavelength $\lambda 2$ and the third predetermined wavelength $\lambda 3$ are on the longer wavelength side than the first predetermined wavelength $\lambda 1$ that is the measurement wavelength, and belong to a wavelength range in which the effect of the light scattering due to the blood cell components or the like is dominant in the total absorbance. The fourth predetermined wavelength $\lambda 4$ and the fifth predetermined wavelength $\lambda 5$ are on the shorter wavelength side than the first predetermined wavelength $\lambda 1$ that is the measurement wavelength, and belong to a wavelength range in which the effect of the light absorption due to hemoglobin is large in the total absorbance.

In other words, as the second actual measurement value D2 and the third actual measurement value D3, the component measurement apparatus 1 uses the absorbance of the mixture X at the second predetermined wavelength $\lambda 2$ and the third predetermined wavelength $\lambda 3$ that belong to a longer wavelength range than the measurement wavelength, for example, that belong to a long wavelength region W1 on a longer wavelength side than the wavelength range W3, in which the measurement wavelength belongs to the wavelength range corresponding to the full width region at half maximum of the peak wavelength region in the absorbance spectrum of the coloring component to be measured.

In addition, as the fourth actual measurement value D4 and the fifth actual measurement value D5, the component measurement apparatus 1 uses the fourth actual measurement value D4 and the fifth actual measurement value D5 that are the absorbance of the mixture X at the fourth predetermined wavelength $\lambda 4$ and the fifth predetermined wavelength $\lambda 5$ belonging to a shorter wavelength range than the measurement wavelength, for example, belonging to a short wavelength region W2 on a shorter wavelength side than the wavelength range W3, in which the measurement wavelength belongs to the wavelength range corresponding to the full width region at half maximum of the peak wavelength region in the absorbance spectrum of the coloring component to be measured.

In the component measurement apparatus 1, the control unit 50 acquires the first actual measurement value D1 to the fifth actual measurement value D5 from the light measurement unit 51. Specifically, the radiation light having light emission wavelengths including the first predetermined wavelength $\lambda 1$ to the fifth predetermined wavelength $\lambda 5$ is applied to the mixture X from the first light source 67 to the fifth light source 68d of the light emitting unit 66. The light receiving unit 72 receives the transmitted light transmitted through the mixture X of the respective radiation light. Further, the control unit 50 calculates the absorbance of the mixture X at each wavelength from the relation between the radiation light and the transmitted light, and stores the first actual measurement value D1 to the fifth actual measurement value D5, which are the absorbance of the mixture X at respective wavelengths, in the storage unit 52 as the actual measurement value data. The control unit 50 can acquire the actual measurement value data from the storage unit 52. A method for the control unit 50 to acquire the first actual measurement value D1 to the fifth actual measurement value D5 is not limited to the method described above, and the first actual measurement value D1 to the fifth actual measurement value D5 can be acquired by various known methods.

Then, the control unit 50 corrects the first actual measurement value D1 using the second actual measurement value D2 to the fifth actual measurement value D5, and estimates the absorbance of the coloring component at the first predetermined wavelength $\lambda 1$ (660 nm in the present embodiment) that is the measurement wavelength. In the long wavelength region W1 where the light scattering due to the blood cell components or the like is dominant, the absorbance spectrum of the mixture X is substantially linear, and thus the component measurement apparatus 1 can estimate to a certain extent the absorbance caused by a disturbance factor (noise) other than the absorbance caused by the coloring component at the first predetermined wavelength $\lambda 1$ that is the measurement wavelength by acquiring the second actual measurement value D2 that is the absorbance at the second predetermined wavelength $\lambda 2$ and the third actual measurement value D3 that is the absorbance at the third predetermined wavelength $\lambda 3$, and then obtaining a slope between the second actual measurement value D2 and the third actual measurement value D3.

In addition, the component measurement apparatus 1 can calculate the concentration of glucose in the sample in consideration of the ratio of the reduced hemoglobin to the oxygenated hemoglobin in the erythrocytes in addition to the optical characteristics of the blood cell components or the like in the sample. Therefore, the component measurement apparatus 1 can perform a more accurate correction by using two wavelengths (the fourth predetermined wavelength and the fifth predetermined wavelength) selected by the ratio of the reduced hemoglobin to the oxygenated hemoglobin.

Specifically, the component measurement apparatus 1 uses a wavelength, as the fourth predetermined wavelength $\lambda 4$, at which the difference in the absorption coefficient between the reduced hemoglobin and the oxygenated hemoglobin is equal to or less than the first predetermined value, and also uses a wavelength, as the fifth predetermined wavelength $\lambda 5$, at which the difference in the absorption coefficient between the reduced hemoglobin and the oxygenated hemoglobin is larger than the first predetermined value. More specifically, the component measurement apparatus 1 uses a wavelength, as the fourth predetermined wavelength $\lambda 4$, at which the ratio of the absorption coefficient of the oxygenated hemoglobin to the absorption coefficient of the reduced hemoglobin is equal to or higher than a first threshold value as a predetermined threshold value, and also uses a wavelength, as the fifth predetermined wavelength $\lambda 5$, at which the ratio of the absorption coefficient of the oxygenated hemoglobin to the absorption coefficient of the reduced hemoglobin is less than the first threshold value. In other words, the component measurement apparatus 1 uses two wavelengths as the fourth predetermined wavelength $\lambda 4$ and the fifth predetermined wavelength $\lambda 5$, that is, a wavelength at which the ratio of the absorption coefficient of the oxygenated hemoglobin to the absorption coefficient of the reduced hemoglobin is equal to or higher than the first threshold and a wavelength at which the ratio of the absorption coefficient of the oxygenated hemoglobin to the absorption coefficient of the reduced hemoglobin is less than the first threshold value. Accordingly, when the control unit 50 corrects the first actual measurement value D1 using the second actual measurement value D2 to the fifth actual measurement value D5, the control unit 50 can perform a more accurate correction in consideration of the ratio of the reduced hemoglobin to the oxygenated hemoglobin.

As the two wavelengths selected by the ratio of the reduced hemoglobin to the oxygenated hemoglobin, it is preferable to use two wavelengths at which the difference in the light absorption due to hemoglobin is large based on the ratio of the reduced hemoglobin to the oxygenated hemoglobin. Therefore, in the present embodiment, a wavelength at which the ratio of the absorption coefficient of the oxygenated hemoglobin to the absorption coefficient of the reduced hemoglobin is 0.8 or more is used as the fourth predetermined wavelength $\lambda 4$. Further, it is preferable to use a wavelength, as the fifth predetermined wavelength $\lambda 5$, at which the ratio of the absorption coefficient of the oxygenated hemoglobin to the absorption coefficient of the reduced hemoglobin is less than 0.8. In the present embodiment, as an example, the fourth predetermined wavelength $\lambda 4$ is 520 nm and the fifth predetermined wavelength $\lambda 5$ is 589 nm.

In this way, in the short wavelength region W2 where the light absorption of the entire hemoglobin fluctuates greatly depending on the ratio of the reduced hemoglobin and the oxygenated hemoglobin, by using the fourth predetermined wavelength $\lambda 4$ and the fifth predetermined wavelength $\lambda 5$ at which the difference in the light absorption of the entire hemoglobin is large, the absorbance due to the noise at the first predetermined wavelength $\lambda 1$ (660 nm in the present embodiment) that is the measurement wavelength can be accurately estimated in consideration of the ratio of the reduced hemoglobin to the oxygenated hemoglobin as well. Therefore, according to the component measurement apparatus 1, it is possible to accurately measure the absorbance of the coloring component at the first predetermined wavelength $\lambda 1$ that is the measurement wavelength, and further accurately measure the component to be measured (the measurement of the concentration of glucose in the present embodiment).

In the present embodiment, only the fourth predetermined wavelength $\lambda 4$ and the fifth predetermined wavelength $\lambda 5$ are wavelengths for which the effect of the ratio of the reduced hemoglobin to the oxygenated hemoglobin is largely taken into consideration, and it is more preferable to use the same wavelengths for the second predetermined wavelength $\lambda 2$ and the third predetermined wavelength $\lambda 3$ in addition to the fourth predetermined wavelength $\lambda 4$ and the fifth predetermined wavelength $\lambda 5$.

Specifically, a wavelength at which the difference in the absorption coefficient between the reduced hemoglobin and the oxygenated hemoglobin is equal to or less than the second predetermined value is used as the second predetermined wavelength $\lambda 2$ in the long wavelength region W1 in which the light scattering due to the blood cell components or the like is dominant, and a wavelength at which the difference in the absorption coefficient between the reduced hemoglobin and the oxygenated hemoglobin is larger than the second predetermined value is used as the third predetermined wavelength $\lambda 3$ in the long wavelength region W1 similarly. More specifically, it is preferable to use a wavelength at which the ratio of the absorption coefficient of the oxygenated hemoglobin to the absorption coefficient of the reduced hemoglobin is equal to or larger than the first threshold value and is equal to or less than a second threshold value as the second predetermined wavelength $\lambda 2$, and to use a wavelength at which the ratio of the absorption coefficient of the oxygenated hemoglobin to the absorption coefficient of the reduced hemoglobin is less than the first threshold value, or a wavelength at which the ratio of the absorption coefficient of the oxygenated hemoglobin to the absorption coefficient of the reduced hemoglobin is larger than the second threshold value as the third predetermined wavelength $\lambda 3$ in the long wavelength region W1 similarly. The second threshold value is another predetermined threshold value that is larger than the first threshold value. That is, it is preferable to use two wavelengths at which the ratio of the absorption coefficient of the oxygenated hemoglobin to the absorption coefficient of the reduced hemoglobin is in a different range as the second predetermined wavelength $\lambda 2$ and the third predetermined wavelength $\lambda 3$. Accordingly, when the control unit 50 corrects the first actual measurement value D1 using the second actual measurement value D2 to the fifth actual measurement value D5, the control unit 50 can perform a highly accurate correction that further considers the ratio of the reduced hemoglobin to the oxygenated hemoglobin.

In particular, in the long wavelength region W1, the effect of the light scattering due to the blood cell components or the like is dominant, but the effect of the light absorption due to hemoglobin is also included to a certain extent as the measurement wavelength of the component to be measured. Accordingly, it is preferable to use two wavelengths at which the light absorption due to hemoglobin changes relatively significantly depending on the ratio of the reduced hemoglobin to the oxygenated hemoglobin as the second predetermined wavelength $\lambda 2$ and the third predetermined wavelength $\lambda 3$.

Therefore, in the present embodiment, as the second predetermined wavelength $\lambda 2$, it is preferable to use a wavelength belonging to a range in which the ratio of the absorption coefficient of the oxygenated hemoglobin to the absorption coefficient of the reduced hemoglobin is 0.8 or more and 1.5 or less. In the present embodiment, as an example, the second predetermined wavelength $\lambda 2$ is 850 nm. Further, the second predetermined wavelength $\lambda 2$ is selected from a range of 790 nm to 850 nm.

The third predetermined wavelength $\lambda 3$ is a wavelength in the long wavelength region W1, and the absorbance of the coloring component included in the total absorbance at the third predetermined wavelength $\lambda 3$ is 10% or less, preferably 6% or less, more preferably 3% or less, and further preferably substantially 0% of the absorbance of the coloring component included in the total absorbance at the measurement wavelength. In other words, it is particularly preferable to use a wavelength equal to or higher than a wavelength that is a tail on a long wavelength side of the peak wavelength region of the absorbance spectrum of the coloring component. Accordingly, it is possible to eliminate the effect of the light absorption of the coloring component and to more accurately estimate the noise in which the effect of the light scattering due to the blood cell components or the like in the long wavelength region W1 is dominant. In the present embodiment, the third predetermined wavelength $\lambda 3$ is a wavelength selected from 920 to 950 nm, and as an example, 940 nm. As the third predetermined wavelength $\lambda 3$, it is particularly preferable to use a wavelength at which the absorbance of the coloring component is zero, that is, a wavelength that is the tail on the long wavelength side of the peak wavelength region of the absorbance spectrum of the coloring component. The "total absorbance" of the "absorbance of the coloring component included in the total absorbance" described above means the absorbance acquired by measuring the mixture containing the sample and/or the coloring component. The "absorbance of the coloring component" of the "absorbance of the coloring component included in the total absorbance" described above means the absorbance of the reaction product that is generated by the color reaction between the component to be measured in the sample and the coloring reagent in the reagent, that is, the absorbance of coloring component.

As described above, the component measurement apparatus 1 can correct the first actual measurement value D1, which is the actual measurement value of the absorbance of the mixture X at the measurement wavelength, using the second actual measurement value D2 to the fifth actual measurement value D5 that are the actual measurement values of the absorbance of the mixture X at the second predetermined wavelength $\lambda 2$ to the fifth predetermined wavelength $\lambda 5$, and can estimate the absorbance of the coloring component at the measurement wavelength.

Next, a method of correction process executed by the control unit 50 of the component measurement apparatus 1 in the first mode will be described.

As described above, the storage unit 52 of the component measurement apparatus 1 stores the actual measurement value data including the first actual measurement value D1 to the fifth actual measurement value D5, which are the absorbance of the mixture X at the first predetermined wavelength $\lambda 1$ to the fifth predetermined wavelength $\lambda 5$ measured by the light measurement unit 51, a group of correction coefficient data that correlates with the absorbance of the mixture X at the second predetermined wavelength $\lambda 2$ to the fifth predetermined wavelength $\lambda 5$, and calibration curve data showing a relation between the absorbance of the coloring component in the mixture X, which is acquired by correcting the absorbance of the mixture X actually measured at the first predetermined wavelength $\lambda 1$ with the correction coefficient data, and various physical quantities.

The control unit 50 derives, based on the actual measurement value data and the correction coefficient data stored in the storage unit 52, the absorbance of the coloring component at the first wavelength $\lambda 1$ that is the measurement wavelength.

Here, the correction coefficient data is derived by regression analysis performed in advance using a formula shown by the following Math (1).

[Math 1]

$$B(\lambda 1)=b0+b1*B(\lambda 2)+b2*B(\lambda 3)+b3*B(\lambda 4)+b4*B(\lambda 5) \qquad (1)$$

$B(\lambda)$ means the absorbance at a wavelength $\lambda$ that is caused by a disturbance factor (noise) other than the absorbance of the coloring component, and a regression calculation is performed by the formula shown by Math (1) using various blood samples so as to derive coefficients b0, b1, b2, b3 and b4. As described above, in the present embodiment, the second predetermined wavelength $\lambda 2$ is 850 nm, the third predetermined wavelength $\lambda 3$ is 940 nm, the fourth predetermined wavelength $\lambda 4$ is 520 nm, and the fifth predetermined wavelength $\lambda 5$ is 589 nm. In addition, as the various blood samples, blood samples respectively having a hematocrit value adjusted to a range of 10% to 70% are prepared based on 6 blood samples with different compositions, absorbance spectra of the adjusted blood samples are measured and the coefficients b0, b1, b2, b3 and b4 are derived using the regression analysis. A group of correction coefficients that correlate with the absorbance of the mixture X at each of the second predetermined wavelength $\lambda 2$ to the fifth predetermined wavelength $\lambda 5$ is derived based on these derived coefficients b0 to b4. By using the correction coefficient data including these correction coefficients, it is possible to correct the actual measurement value of the absorbance of the mixture X at 660 nm, which is the measurement wavelength, from the actual measurement values of the absorbance of the mixture X at 520 nm, 589 nm, 850 nm and 940 nm, and to estimate the absorbance of the coloring component at 660 nm.

In addition, in order to obtain a blood glucose level more easily, it is also possible to simplify the above formula, correct the actual measurement value of the absorbance of the mixture X at 660 nm, which is the measurement wavelength, from the actual measurement values of the absorbance of the mixture X with respect to light at 520 nm as the fourth predetermined wavelength $\lambda 4$ and light at 850 nm as the second predetermined wavelength $\lambda 2$, and estimate the absorbance of the coloring component at 660 nm.

FIG. 9 is a flowchart showing an example of a component measurement process executed by the component measurement apparatus 1. As shown in FIG. 9, the component measurement process includes: a step S1 of acquiring the first actual measurement value D1 that is the absorbance of the mixture X at the first predetermined wavelength $\lambda 1$ as the measurement wavelength, the second actual measurement value D2 that is the absorbance of the mixture X at the second predetermined wavelength $\lambda 2$, the third actual measurement value D3 that is the absorbance of the mixture X at the third predetermined wavelength $\lambda 3$, the fourth actual measurement value D4 that is the absorbance of the mixture X at the fourth predetermined wavelength λ4, and the fifth actual measurement value D5 that is the absorbance of the mixture X at the fifth predetermined wavelength λ5; a step S2 of deriving a hematocrit value using at least one of the first actual measurement value D1 to the fifth actual measurement value D5; a step S3 of correcting the first actual measurement value D1 using the second actual measurement value D2 to the fifth actual measurement value D5 and the correction coefficients obtained by the regression calculation, and acquiring the absorbance of the coloring component at the first predetermined wavelength λ1 as the measurement wavelength; and a step S4 of calculating the component to be measured in the sample from the absorbance of the coloring component at the first predetermined wavelength λ1 as the measurement wavelength and the derived hematocrit value.

In step S1, as described above, the light emitting unit 66 and the light receiving unit 72 of the light measurement unit 51 are used to acquire the first actual measurement value D1 to the fifth actual measurement value D5. In the present embodiment, in step S2, the hematocrit value is derived based on the fourth actual measurement value D4 or based on the fourth actual measurement value D4 and the second actual measurement value D2. Specifically, in step S2, the absorbance due to hemoglobin is estimated from the fourth actual measurement value D4 or from the fourth actual measurement value D4 and the second actual measurement value D2, and the hematocrit value is derived. Further, when the fourth actual measurement value D4, or the fourth actual measurement value D4 and the second actual measurement value D2 include the absorption of the coloring component, the hematocrit value is derived from a correction value obtained by performing a correction calculation that subtracts the absorption of the coloring component from the fourth actual measurement value D4 or the fourth actual measurement value D4 and the second actual measurement value D2, respectively. In the present embodiment, the hematocrit value is derived from the calibration curve stored in the storage unit 52 that shows the relation between the absorbance of hemoglobin in the mixture X and the hematocrit value. In step S3, the first actual measurement value D1 is actually corrected using the second actual measurement value D2 to the fifth actual measurement value D5 and the correction coefficients obtained by the regression calculation, and the absorbance of the coloring component at the first measurement wavelength is estimated and acquired. In addition, when the second actual measurement value D2 to the fifth actual measurement value D5 include the absorption of the coloring component, by performing a recalculation, the absorbance of the coloring component at the first predetermined wavelength λ1 is estimated and is acquired from the correction value obtained by performing the correction calculation that subtracts the absorption of the coloring component from each of the measurement values. Finally, in step S4, the concentration of glucose is calculated using the calibration curve showing the relation with the concentration of glucose from the acquired absorbance of the coloring component at the first predetermined wavelength λ1 that is the measurement wavelength and from the derived hematocrit value.

When the component measurement process is executed, the control unit 50 of the component measurement apparatus 1 causes the radiation light to be emitted from the first light source 67 to the fifth light source 68d according to a predetermined algorithm, and the light receiving unit 72 measures the intensity of received light. Hereinafter, details of a light amount measurement process executed by the control unit 50 when the component measurement process is executed will be described.

FIG. 10 is a flowchart showing an example of the light amount measurement process executed by the component measurement apparatus 1 during the component measurement process. The flow of FIG. 10 is executed, for example, when the operator inputs the processing mode and inputs a start instruction of the process. Here, a case in which the operator selects the first mode of measuring the component to be measured as the processing mode will be described below.

Here, while executing the component measurement process, the control unit 50 causes the first light source 67 to the fifth light source 68d to emit the radiation light by setting processes in which the radiation light is sequentially emitted once as pulsed light as one set. FIG. is a diagram schematically showing one set of the radiation light emitted from the first light source 67 to the fifth light source 68d, and is a graph showing intensities of the received light of the radiation light emitted from the first light source 67 to the fifth light source 68d, which are measured by the light receiving unit 72. In FIG. 11, a horizontal axis represents the time and a vertical axis represents the intensity of received light. As shown in FIG. 11, the control unit 50 causes the first light source 67 to the fifth light source 68d to sequentially emit light at predetermined time intervals. In an example shown in FIG. 11, the control unit 50 causes the first light source 67 to the fifth light source 68d to emit light every 1 msec as the predetermined time intervals. Further, as shown in FIG. 11, the control unit 50 causes the first light source 67 to the fifth light source 68d to emit light such that the intensity of received light in the light receiving unit 72 of each radiation light from the first light source 67 to the fifth light source 68d is approximately the same intensity. The approximately same intensity means that a difference in the intensity of received light obtained from the light emission of the light sources does not affect a result of the component measurement process when the component measurement process is executed with the intensity of received light in the light receiving unit 72.

Here, the control unit 50 causes the first light source 67 to the fifth light source 68d to emit light in a predetermined order in one set of emission processes. In particular, the control unit 50 causes the second light source 68a and the third light source 68b to emit light at timings before and after a timing for causing the first light source 67 to emit light. The second light source 68a and the third light source 68b emit radiation light of the second predetermined wavelength λ2 and radiation light of the third predetermined wavelength λ3 at which the effect of the light scattering due to the blood cell components or the like is dominant, and the first light source 67 emits pulsed light of the first predetermined wavelength λ1 that is the measurement wavelength.

In the example shown in FIG. 11, the control unit 50 causes the fifth light source 68d, the third light source 68b, the first light source 67, the second light source 68a, and the fourth light source 68c to subsequentially emit the radiation light to the measurement region in one set of emission processes. Therefore, the light receiving unit subsequentially receives the radiation light of the fifth predetermined wavelength λ5, the radiation light of the third predetermined wavelength λ3, the radiation light of the measurement wavelength (the first predetermined wavelength λ1), the radiation light of the second predetermined wavelength λ2, and the radiation light of the fourth predetermined wavelength λ4 every predetermined time interval (1 msec). The light scattering due to the blood cell components fluctuates with the elapse of time due to effects of Brownian motion and sedimentation of molecules, further interference as wave properties, and the like. Therefore, it is preferable that the second actual measurement value D2 and the third actual measurement value D3 used for correcting the effect caused by the light scattering are acquired at a timing that is temporally closer to the first actual measurement value D1 to be corrected. This is because the acquisition at the timing that is temporally closer makes it less susceptible to a temporal fluctuation. Therefore, as in the present embodiment, the effect caused by the light scattering can be corrected with higher accuracy by causing the second light source 68a and the third light source 68b to emit light at the timings before and after the timing for causing the first light source 67 to emit light, in which the second light source 68a and the third light source 68b emit the radiation light of the second predetermined wavelength $\lambda 2$ and the radiation light of the third predetermined wavelength $\lambda 3$ at which the effect of the light scattering due to the blood cell components or the like is dominant, and the first light source 67 emits the pulsed light of the first predetermined wavelength $\lambda 1$ that is the measurement wavelength.

In addition, the control unit 50 does not necessarily cause the fifth light source 68d, the third light source 68b, the first light source 67, the second light source 68a, and the fourth light source 68c to subsequentially emit the radiation light in one set of emission processes. The control unit 50 may cause the second light source 68a and the third light source 68b to emit light at the timings before and after the timing for causing the first light source 67 to emit light.

Referring to FIG. 10, for example, when the control unit 50 detects an operation input for starting the process by the operator of the component measurement apparatus 1, the control unit 50 starts to cause the first light source to the fifth light source 68d to emit the radiation light (step S11). At this time, the control unit 50 causes the first light source 67 to the fifth light source 68d to emit the radiation light so that the control unit 50 can detect whether the component measurement chip 2 is mounted on the component measurement apparatus 1.

FIG. 12 is a diagram schematically showing the intensities of received light of the radiation light emitted from the first light source 67 to the fifth light source 68d in step S11 of FIG. 10, which is measured by the light receiving unit 72. In FIG. 12, the horizontal axis represents the time and the vertical axis represents the intensity of received light. As schematically shown in FIG. 12, the control unit 50 repeatedly outputs the set of emission processes described with reference to FIG. 11. For example, the control unit 50 repeatedly executes the set of emission processes 1 to 200 times per second. In the present embodiment, the set of emission processes is repeatedly executed 16 times per second. The control unit 50 stops the output of the radiation light after repeating the set of emission processes 16 times. Then, the control unit 50 repeatedly outputs the set of emission processes 16 times again without interruption after a predetermined time (here, 1 second) elapsed from the start of the set of emission processes for 16 times. The control unit 50 stops the output of the radiation light again after repeating the set of emission processes for 16 times. In this way, the control unit 50 repeats a combination of the output of the set of emission processes for 16 times and the stop of the output of the radiation light every second until step S14 to be described below.

Next, the control unit 50 determines a first intensity of received light (step S12). Specifically, in a determination process of the first intensity of received light, the control unit 50 determines whether the intensity of received light in the light receiving unit 72 is within a normal range (step S12).

Here, details of the determination process of the first intensity of received light executed by the control unit 50 in step S12 will be described. The determination process of the first intensity of received light is the process of detecting whether the normal measurement can be executed described above, which is executed by the control unit 50. FIG. 13 is a flowchart showing an example of the determination process of the first intensity of received light.

The control unit 50 executes two determination processes in the determination process of the first intensity of received light, that is, in the process of detecting whether the normal measurement can be executed. One is the determination process based on an absolute output value output from the light receiving unit 72, and the other is the determination process based on a relative output value output from the light receiving unit 72. The determination process based on the absolute output value is executed from step S31 to step S35 of the flow of FIG. 13, and the determination process based on the relative output value is executed from step S36 to step S40 of the flow of FIG. 13.

The absolute output value here is an output value from an AD converter connected to the light receiving unit 72 in response to the intensity of received light in the light receiving unit 72 when no light is emitted from the light emitting unit 66 (the first light source 67 to the fifth light source 68d). The relative output value is a difference between an output value from the AD converter connected to the light receiving unit 72 when the light is emitted from the light emitting unit 66 (the first light source 67 to the fifth light source 68d) and the output value from the AD converter connected to the light receiving unit 72 when no light is emitted from the light emitting unit 66 (the first light source 67 to the fifth light source 68d). That is, the relative output value is obtained by subtracting an output value A observed when the light emitting unit 66 does not emit light from an output value R' observed when the light emitting unit 66 emits light. An absolute output value A and a relative output value R are obtained and calculated while the light emitting unit 66 repeatedly turns on and off. For example, as indicated by arrows in FIG. 11, a relative output value R5 at the fifth predetermined wavelength $\lambda 5$ is acquired at a predetermined timing while the radiation light of the fifth predetermined wavelength $\lambda 5$ is emitted, and an absolute output value A5 at the fifth predetermined wavelength $\lambda 5$ is acquired at a timing when no radiation light is emitted, which is a timing before the predetermined timing by a predetermined time. The same applies to the first predetermined wavelength $\lambda 1$ to the fourth predetermined wavelength $\lambda 4$. The absolute output value and the relative output value here are obtained from a plurality of absolute output values and a plurality of relative output values acquired within a predetermined section with respect to a light source having the same wavelength, by using a moving average.

In the present embodiment, it is assumed that an AD converter having a resolution of 12 bits is used as the converter. However, the resolution of the AD converter is not necessarily to be 12 bits, and an AD converter having an appropriate resolution may be used. Further, a value of the AD converter having a resolution of 12 bits can be converted into an output value of the AD converter having another resolution.

As the determination process based on the absolute output value, the control unit 50 first acquires an absolute output value in response to the intensity of received light from the light receiving unit 72 (step S31). Specifically, the light receiving unit 72 outputs an output value in response to the intensity of received light from the AD converter, and the control unit 50 acquires the output value output from the AD converter. In step S31, the control unit 50 acquires the absolute output value. The absolute output value can be obtained from intensities of received light acquired at a plurality of timings when the light emitting unit 66 does not emit light, by using the moving average. The number of times of averaging processes may be set appropriately.

Next, the control unit 50 determines whether the acquired absolute output value is within a predetermined range. Specifically, the control unit 50 determines whether the acquired absolute output value is within, for example, a first specified range of the absolute output value that is set in advance (step S32). By executing step in this way, the control unit 50 determines whether there is an abnormality in the light receiving unit 72 and/or a circuit connected to the light receiving unit 72 before starting a measurement process of a substance to be measured. Therefore, the first specified range is set as a range in which the absolute output value of the intensity of received light in the light receiving unit 72 output from the AD converter is recognized as in a normal range. That is, the first specified range reflects the presence or absence of abnormality in the light receiving unit 72 and the circuit connected to the light receiving unit 72. The first specified range can be appropriately determined according to specifications and the like of the component measurement apparatus 1. For example, as in the present embodiment, when the 12-bit AD converter is used, the first specified range can be 51 or more and 3900 or less. The first specified range is not limited to the example shown here, and may be appropriately determined.

When the control unit 50 determines that the acquired absolute output value is not included in the first specified range (NO in step S32), the control unit 50 determines whether the acquired absolute output value is below a lower limit value of the first specified range (step S33). For example, when the first specified range is 51 or more and 3900 or less, the control unit 50 determines in step S33 whether the acquired absolute output value is 50 or less.

When the control unit 50 determines that the acquired absolute output value is below the lower limit value of the first specified range (YES in step S33), the control unit 50 determines that an abnormality in the circuit connected to the light receiving unit 72 (a circuit abnormality) occurs (step S34). In this example here, the case in which the absolute output value is below the lower limit value of the first specified range is a case in which the absolute output value is 0 or more and 50 or less. In this case, because the intensity of received light in the light receiving unit 72 output from the AD converter is lower than the first specified range recognized as a normal range, it is highly probable that a leakage current or the like that affects the measurement occurs. Therefore, the control unit 50 determines that an abnormality of a reference voltage (the circuit abnormality) or the like occurs.

On the other hand, when the control unit 50 determines that the acquired absolute output value is not below the lower limit value of the first specified range (NO in step S33), the control unit 50 determines that an abnormality in sensitivity of received light caused by an abnormality in the light receiving unit 72 or an abnormality in the circuit connected to the light receiving unit 72 occurs (step S35). When the absolute output value is not below the lower limit value of the first specified range, the acquired absolute output value exceeds an upper limit value of the first specified range because the control unit 50 determines in step S32 that the absolute output value is not within the first specified range. That is, in this example, the case in which the absolute output value is not below the lower limit value of the first specified range is a case in which the absolute output value is 3901 or more and 4095 or less. In this case, because the intensity of received light in the light receiving unit 72 output from the AD converter is higher than the first specified range recognized as a normal range, it is highly probable that a structural failure of the light receiving unit 72, current interruption or the like that affects the measurement occurs. Therefore, the control unit 50 determines that the abnormality in the sensitivity of received light occurs. In step S35, in addition to the abnormality in the sensitivity of received light, it is also possible to detect a breakage of the tip end opening 10*s* of the component measurement apparatus 1 before mounting the component measurement chip 2.

When the control unit 50 determines in step S34 that the circuit abnormality such as the abnormality of the reference voltage occurs, or when the control unit 50 determines in step S35 that the abnormality in the sensitivity of received light occurs, the control unit 50 determines in step S12 of FIG. 10 that the intensity of received light is not within the normal range (NO in step S12). In such a case, the control unit 50 reports an error, for example, by outputting a buzzer sound from the buzzer unit 59 (step S23). The control unit 50 may output an error according to the type of the determined abnormality. For example, the control unit 50 may output a different buzzer sound according to the type of the determined abnormality, or may report the type of the determined abnormality by voice. The control unit 50 may report the type of the determined abnormality by displaying the type of the determined abnormality on the display unit 11. When an error occurs, the control unit 50 may stop the process. The control unit 50 stops the measurement process of the component to be measured after reporting the error. Accordingly, when there is a possibility of an abnormality, the process will not be executed. The same applies to a case of reporting an error to be described below.

When the control unit 50 determines in step S32 that the acquired absolute output value is included in the first specified range (YES in step S32), the control unit 50 determines no abnormality found in the determination process based on the absolute output value, that is, determines that the determination process is normal, and starts the determination process based on the relative output value. Specifically, the control unit 50 proceeds to a process of step S36.

As the determination process based on the relative output value, the control unit 50 acquires a relative output value in response to the intensity of received light from the light receiving unit 72 (step S36). Specifically, the light receiving unit 72 outputs the output value in response to the intensity of received light from the AD converter, and the control unit 50 acquires the output value output from the AD converter. In step S36, the control unit 50 calculates and acquires the relative output value based on the output value output from the AD converter.

Next, the control unit 50 determines whether the acquired relative output value is within a predetermined range. Specifically, the control unit 50 determines whether the acquired relative output value is within, for example, a second specified range of the relative output value that is set in advance (step S37). The second specified range is a range in which the relative output value of the intensity of received light in the light receiving unit 72 output from the AD converter is recognized as in a normal range. The second specified range can be appropriately determined according to the specifications and the like of the component measurement apparatus 1. For example, as in the present embodiment, when the 12-bit AD converter is used, the second specified range can be 601 or more and 3900 or less. The second specified range is not limited to the example shown here, and may be appropriately determined. By this step, the control unit 50 can detect an abnormality in the light emitting unit 66 or the optical path before the component measurement chip 2 is inserted into the component measurement apparatus 1.

When the control unit 50 determines that the acquired relative output value is not included in the second specified range (NO in step S37), the control unit 50 determines whether the acquired relative output value is below a lower limit value of the second specified range (step S38). For example, when the second specified range is 601 or more and 3900 or less, the control unit 50 determines in step S38 whether the acquired relative output value is 600 or less.

When the control unit 50 determines that the acquired relative output value is below the lower limit value of the second specified range (YES in step S38), the control unit 50 determines that an abnormality due to insufficient light amount caused by dirt on the light measurement unit 51 or an output reduction of the light emitting unit 66 occurs (step S39). The abnormality due to insufficient light amount includes a fact that the amount of light emitted from the light emitting unit 66 is insufficient and a fact that the light receiving unit 72 cannot detect a sufficient amount of light required for measuring an object to be measured. The dirt on the light measurement unit 51 indicates dirt (adhesion of foreign matter) that blocks light in anywhere of the optical path from the light emitting unit 66 to the light receiving unit 72. For example, the light from the light emitting unit 66 is blocked because the cover member 25 is dirty. Further, the output reduction of the light emitting unit 66 indicates an abnormality in the light source itself or an abnormality in a circuit connected to the light emitting unit 66. In this example, the case in which the relative output value is below the lower limit value of the second specified range is a case in which the relative output value is 0 or more and 600 or less. In such a case, a difference between an output from the AD converter when the light is emitted from the light emitting unit 66 (the first light source 67 to the fifth light source 68*d*) and an output from the AD converter when no light is emitted from the light emitting unit 66 (the first light source 67 to the fifth light source 68*d*) is equal to or less than a predetermined value, and thus it is highly probable that the dirt of the light measurement unit 51 or the output reduction of the light emitting unit 66 occurs. Therefore, the control unit 50 determines that the abnormality due to insufficient light amount occurs.

On the other hand, when the control unit 50 determines that the acquired relative output value is not below the lower limit value of the second specified range (NO in step S38), the control unit 50 determines that an abnormality in light emitting amount caused by excessive light emitting amount occurs (step S40). When the relative output value is not below the lower limit value of the second specified range, the acquired relative output value exceeds an upper limit value of the second specified range because the control unit 50 determines in step S37 that the relative output value is not within the second specified range. That is, in this example, the case in which the relative output value is not below the lower limit value of the second specified range is a case in which the relative output value is 3901 or more and 4095 or less. In this case, because the intensity of received light in the light receiving unit 72 output from the AD converter is higher than the second specified range recognized as a normal range, it is highly probable that a higher amount of light than a light emitting amount of light that can be received by the light receiving unit 72 is emitted from the LED. That is, it is highly probable that an overcurrent to the LED is generated due to the abnormality in the circuit connected to the light emitting unit 66. Therefore, the control unit 50 determines that the abnormality in light emitting amount occurs.

When the control unit 50 determines in step S39 that the abnormality due to insufficient light amount occurs, or when the control unit 50 determines in step S40 that the abnormality in light emitting amount occurs, the control unit 50 determines in step S12 of FIG. 10 that the intensity of received light is not within the normal range (NO in step S12). In such a case, the control unit 50 reports an error, for example, by outputting a buzzer sound from the buzzer unit 59 (step S23). A mode of error reporting may be the same as in the above example. Accordingly, it is possible to inform the operator of whether the component measurement apparatus 1 is in a normal measurement operation state before the component measurement chip 2 is actually inserted into the component measurement apparatus 1. Because the operator can stop the measurement operation at a stage in which the error is reported, extra consumption of the component measurement chip 2 and blood collection can be prevented.

When the control unit 50 determines in step S37 that the acquired relative output value is included in the second specified range (YES in step S37), the control unit 50 determines no abnormality found in the determination process based on the relative output value, that is, the determination process is normal.

When the control unit 50 determines in step S32 that the acquired absolute output value is included in the first specified range (YES in step S32), and determines in step S37 that the acquired relative output value is included in the second specified range (YES in step S37), the control unit 50 determines in step S12 of FIG. 10 that the intensity of received light is in the normal range (YES in step S12). Then, the control unit 50 proceeds to step S13 of the flow of FIG. 10. When step S13 of the flow of FIG. 10 is not executed, the control unit 50 proceeds to step S14.

In this way, the control unit 50 according to the present embodiment can execute the process of detecting whether the normal measurement can be executed by the component measurement apparatus 1. When the control unit 50 determines that an abnormality may occur in the component measurement apparatus 1, the control unit 50 can inform the operator of the possibility of an abnormality by reporting the fact. Further, by outputting an error depending on the type of the determined abnormality, the control unit 50 can also inform the operator of the type of the error.

In the example described with reference to FIG. 13, the case in which the control unit 50 executes the determination process based on the absolute output value and the determination process based on the relative output value is described. However, the control unit 50 does not necessarily execute both the determination process based on the absolute output value and the determination process based on the relative output value. For example, the control unit 50 can detect at least a part of the abnormality by executing at least one of the determination process based on the absolute output value and the determination process based on the relative output value.

Further, as described in the example described with reference to FIG. 13, the control unit 50 executes the determination process based on the relative output value after executing the determination process based on the absolute output value. However, the determination process based on the absolute output value and the determination process based on the relative output value may not be executed in this order. For example, the control unit 50 may execute the determination process based on the absolute output value after executing the determination process based on the relative output value, and may continuously or simultaneously execute the determination process based on the absolute output value and the determination process based on the relative output value.

Referring back to FIG. 10, when the control unit 50 determines that the intensity of received light in the light receiving unit 72 is within the normal range (YES in step S12), the control unit 50 determines whether the component measurement chip 2 is inserted into the chip insertion space S based on a change in the intensity of received light in the light receiving unit 72. Specifically, the control unit 50 determines whether the component measurement chip 2 is inserted into the chip insertion space S in step S14. Alternatively, the control unit 50 may determine whether the component measurement chip 2 is inserted into the chip insertion space S in steps S13 and S14.

More specifically, for example, the operator mounts the component measurement chip 2 on the component measurement apparatus 1. That is, the operator inserts the component measurement chip 2 into the chip mounting space S of the component measurement apparatus 1. When the component measurement chip 2 is inserted into the chip mounting space S, at least a part of the radiation light emitted from the first light source 67 to the fifth light source 68*d* is absorbed by a member constituting the component measurement chip 2 and does not reach the light receiving unit 72. Then, when the component measurement chip 2 is mounted on the component measurement apparatus 1 and the states illustrated in FIGS. 2 and 3 are achieved, an optical path is formed between the first light source 67 to the fifth light source 68*d* and the light receiving unit 72 through a part of the component measurement chip 2. The part of the component measurement chip 2 where the optical path is formed is the measurement spot. In the present embodiment, the measurement reagent 22 is located halfway the optical path. That is, the measurement spot is located on the measurement reagent 22. Therefore, of the radiation light emitted from the first light source 67 to the fifth light source 68*d* toward the measurement region, only a part of the light transmitted through the measurement reagent 22 is received by the light receiving unit 72. That is, when the component measurement chip 2 is mounted on the component measurement apparatus 1, there is a difference in the intensity of received light in the light receiving unit 72 as compared with a case in which the component measurement chip 2 is not mounted.

As a result, the control unit 50 determines whether the component measurement chip 2 is mounted on the component measurement apparatus 1 by detecting the change in the intensity of received light in the light receiving unit 72. The control unit 50 determines that the component measurement chip 2 is inserted into the chip mounting space S when it is detected that the intensity of received light in the light receiving unit 72 is within a predetermined range, in which the component measurement chip 2 is presumed to be inserted into the chip mounting space S, after the amount of light received in the light receiving unit 72 is less than a predetermined amount (that is, a state in which at least a part of the radiation light is blocked by the member constituting the component measurement chip 2 and does not reach the light receiving unit 72).

In the present embodiment, the control unit 50 determines that the component measurement chip 2 is inserted into the chip mounting space S when it is detected that the intensity of received light in the light receiving unit 72 is within the predetermined range in which the component measurement chip 2 is presumed to be inserted into the chip mounting space S based on the intensity of received light in the light receiving unit before the component measurement chip 2 is inserted into the chip insertion space S (step S14).

When the component measurement chip 2 is formed of a light-shielding member except for a portion to be measured, the control unit 50 may detect that the intensity of received light is within the predetermined range after no light is detected by the light receiving unit 72 (that is, the state in which the radiation light is blocked by the member constituting the component measurement chip 2 and does not reach the light receiving unit 72), and determines whether the component measuring chip 2 is inserted. In this case, first, the control unit 50 determines whether the light receiving unit 72 is in the state in which no radiation light is received (step S13). In the present description, the state in which no radiation light is received includes a case in which the amount of light having an intensity of received light that can be detected in the light receiving unit 72 is detected when the radiation light emitted from the first light source 67 to the fifth light source 68*d* is blocked by the component measurement chip 2. Whether the light receiving unit 72 is in the state in which no radiation light is received can be determined, for example, by setting a threshold value in advance and determining whether an output value of the intensity of received light in the light receiving unit 72 from an AD converter is below the threshold value. When the control unit 50 determines that the light receiving unit 72 is not in the state in which no radiation light is received (NO in step S13), the control unit 50 repeats step S13 until it is determined that the light receiving unit 72 is in the state in which no radiation light is received. When the control unit 50 determines that the light receiving unit 72 is in the state in which no radiation light is received (YES in step S13), the control unit 50 determines a second intensity of received light (step S14). In addition, step S13 may be omitted and steps S12 and S14 may be executed.

The determination process of the second intensity of received light is a process of determining whether the component measurement chip 2 is mounted on (inserted into) the component measurement apparatus 1. Further, by the determination process of the second intensity of received light, the control unit 50 can detect whether the normal measurement can be executed. That is, the determination process of the second intensity of received light also serves as the process of detecting whether the normal measurement can be executed.

Here, details of the determination process of the second intensity of received light executed by the control unit 50 in step S14 will be described. FIG. 14 is a flowchart showing an example of the determination process of the second intensity of received light.

The control unit 50 executes two determination processes in the determination process of the second intensity of received light. One is the determination process based on an absolute output value output from the light receiving unit 72, and the other is the determination process based on a relative output value output from the light receiving unit 72. The determination process based on the absolute output value is executed from step S51 to step S57 of the flow of FIG. 14, and the determination process based on the relative output value is executed from step S58 to step S61 of the flow of FIG. 14.

As the determination process based on the absolute output value, the control unit 50 first acquires an absolute output value in response to the intensity of received light from the light receiving unit 72 (step S51).

Next, the control unit 50 determines whether the acquired absolute output value is within a predetermined range. Specifically, the control unit 50 determines whether the acquired absolute output value is within, for example, a third specified range of the absolute output value that is set in advance (step S52). The third specified range is a range in which the absolute output value of the intensity of received light in the light receiving unit 72 output from the AD converter in the state in which the component measurement chip 2 is inserted into the mounting space S is recognized as in a normal range. That is, when the measurement spot of the component measurement chip 2 is located in the optical path and the light emitting unit 66 is not turned on, a range of the intensity of received light in the light receiving unit 72 corresponds to the third specified range. Therefore, an upper limit value of the third specified range is lower than the upper limit value of the first specified range. In step S52, in addition to the presence or absence of abnormality in the light receiving unit 72 and the circuit connected to the light receiving unit 72, the control unit can confirm whether excessive light enters from the outside after the component measurement chip 2 is inserted into the component measurement apparatus 1. That is, by using the third specified range as a reference, the control unit 50 can detect an abnormality in the amount of light from the outside of the component measurement apparatus 1 in addition to the abnormality detected based on the first specified range. The third specified range can be appropriately determined according to specifications and the like of the component measurement apparatus 1 and the component measurement chip 2. For example, as in the present embodiment, when the 12-bit AD converter is used, the third specified range can be 51 or more and 200 or less. However, the third specified range is not limited to the example shown here, and may be appropriately determined.

When the control unit 50 determines that the acquired absolute output value is not included in the third specified range (NO in step S52), the control unit 50 determines whether the acquired absolute output value is below a lower limit value of the third specified range (step S53). For example, when the third specified range is 51 or more and 200 or less, the control unit 50 determines in step S53 whether the acquired absolute output value is 50 or less.

When the control unit 50 determines that the acquired absolute output value is below the lower limit value of the third specified range (YES in step S53), the control unit determines that the circuit abnormality such as the abnormality of the reference voltage caused by the abnormality of the circuit connected to the light receiving unit 72 occurs (step S54). In this example, the case in which the absolute output value is below the lower limit value of the third specified range is the case in which the absolute output value is 0 or more and 50 or less. In this case, because the intensity of received light in the light receiving unit 72 output from the AD converter is lower than the first specified range recognized as the normal range, it is highly probable that the leakage current or the like that affects the measurement occurs. Therefore, the control unit 50 determines that the circuit abnormality occurs.

When the control unit 50 determines that the acquired absolute output value is not below the lower limit value of the third specified range (NO in step S53), the control unit 50 determines whether the acquired absolute output value is included in a fourth specified range of the absolute output value (step S55). The fourth specified range is a range in which abnormal light from the outside or the like is recognized as included in the light received by the light receiving unit 72. In step S55, the control unit 50 can confirm whether there is abnormal light from the light emitting unit 66, and can also determine whether there is an effect due to disturbance light after the component measurement chip 2 is inserted into the component measurement apparatus 1. The disturbance light is light that reaches the light receiving unit 72 from the outside of the component measurement apparatus set 100 when the substance to be measured is measured. For example, the breakage of the tip end opening 10s of the chip mounting portion 10b or breakage of the component measurement chip 2 causes light from the outside generated by, for example, lighting in a measurement environment to enter the chip mounting space S in excess of a predetermined amount, and light corresponding to an amount of the substance to be measured cannot be accurately detected by the light receiving unit 72. In step S55, in this way, it is possible to detect whether there is an effect due to the disturbance light that can affect the measurement of the substance to be measured.

The fourth specified range can be appropriately determined according to the specifications and the like of the component measurement apparatus 1 and the component measurement chip 2. A lower limit value of the fourth specified range is a value larger than the upper limit value of the third specified range, and is set to a value continuous from the upper limit value of the third specified range. For example, as in the present embodiment, when the third specified range is 51 or more and 200 or less, the fourth specified range can be 201 or more and 3900 or less. The fourth specified range is not limited to the example shown here, and may be appropriately determined.

When the control unit 50 determines that the acquired absolute output value is included in the fourth specified range of the absolute output value (YES in step S55), the control unit 50 determines that the disturbance light exceeding the predetermined amount reaches the light receiving unit 72, and determines that an abnormality due to the disturbance light occurs (step S56). In this example, the control unit 50 determines that the abnormality due to the disturbance light occurs when the acquired absolute output value is 201 or more and 3900 or less.

On the other hand, when the control unit 50 determines that the acquired absolute output value is not included in the fourth specified range of the absolute output value (NO in step S55), the control unit 50 determines that the abnormality in the sensitivity of received light caused by the abnormality in the light receiving unit and the abnormality in the circuit connected to the light receiving unit 72 occurs (step S57). In step S54, when the absolute output value is not included in the fourth specified range, the absolute output value exceeds an upper limit value of the fourth specified range. That is, in this example, the case in which the absolute output value is not included in the fourth specified range is a case in which the absolute output value is 3901 or more and 4095 or less. In this case, because the intensity of received light in the light receiving unit 72 output from the AD converter is higher than the fourth specified range recognized as a normal range, it is highly probable that the structural failure of the light receiving unit, the current interruption (a state in which no current flows) or the like that affects the measurement occurs. Therefore, the control unit 50 determines that the abnormality in the sensitivity of received light occurs.

When the control unit 50 determines in step S54 that the circuit abnormality occurs, or when the control unit 50 determines in step S56 that the abnormality due to the disturbance light occurs, or when the control unit 50 determines in step S57 that the abnormality in the sensitivity of received light occurs, the control unit 50 determines in step S14 of FIG. 10 that the intensity of received light is not within the normal range (NO in step S14). In such a case, the control unit 50 reports an error, for example, by outputting a buzzer sound from the buzzer unit 59 (step S23). The mode of error reporting may be the same as in the above example. The control unit 50 can detect whether the normal measurement can be executed by reporting an error when there is a possibility of an abnormality in this way.

When the control unit 50 determines in step S52 that the acquired absolute output value is included in the third specified range (YES in step S52), the control unit 50 determines no abnormality found in the determination process based on the absolute output value, that is, determines that the determination process is normal, and starts the determination process based on the relative output value. Specifically, the control unit 50 proceeds to a process of step S58.

In the determination process based on the relative output value, the control unit 50 determines whether the component measurement chip 2 is appropriately inserted into the component measurement apparatus 1. That is, the control unit 50 determines whether the component measurement chip 2 is inserted into the component measurement apparatus 1 such that the measurement can be normally started. First, the control unit 50 acquires a relative output value in response to the intensity of received light from the light receiving unit 72 (step S58).

Next, the control unit 50 calculates a determination value (step S59). The determination value is a numerical value to be used in the determination in steps S60 and S61, and is a value obtained by dividing a relative output value after the component measurement chip 2 is inserted by a relative output value before the component measurement chip 2 is inserted. That is, the determination value is a value acquired by dividing the relative output value acquired in step S58 by the relative output value (a blank value) acquired in step S36. The relative output value before the component measurement chip 2 is inserted may be automatically adjusted, for example, in a manufacturing process of the component measurement apparatus 1. In a normal case in which there is no dirt (foreign matter adhesion) or the like in the optical path, the relative output value is a value close to the adjusted relative output value. For example, when a target value in the adjustment of the relative output value is set to 2000 and the relative output value acquired in step S36 is also 2000, assuming that the relative output value acquired in step S58 is Vr, a determination value V is calculated by V=Vr/2000 in step S59.

The control unit 50 determines whether the determination value V calculated in step S59 is included in a fifth specified range (step S60). The fifth specified range is a range in which the component measurement chip 2 is recognized as being appropriately inserted into the component measurement apparatus 1. That is, when the determination value V is within the fifth specified range, the control unit 50 can recognize that the component measurement chip 2 is mounted on the component measurement apparatus 1 and the measurement spot is disposed in the optical path. The fifth specified range can be appropriately determined according to the specifications and the like of the component measurement apparatus 1 and the component measurement chip 2 in an appropriate mode. In the present embodiment, the fifth specified range is set to 0.05 or more than 0.05 and 0.3 or less. That is, the fifth specified range corresponds to a case in which, with respect to the relative output value (the amount of the received light) before the component measurement chip 2 is inserted into the component measurement apparatus 1, the relative output value (the amount of the received light) after the component measurement chip 2 is inserted into the component measurement apparatus 1 is more than 5% and 30% or less. The fifth specified range is a range in which, in the component measurement chip 2 before the sample is introduced, the intensity of the light transmitted through the measurement reagent 22 is reflected.

When the control unit 50 determines that the determination value V is included in the fifth specified range, that is, $0.05 < V \leq 0.3$ (YES in step S60), the control unit 50 determines that the component measurement chip 2 is appropriately inserted into the component measurement apparatus 1. This determination result is hereinafter also simply referred to as "chip normality recognition" in the present description. In such a case, the control unit 50 determines in step S14 of FIG. 10 that the intensity of received light is within the normal range (YES in step S14). Then, the control unit 50 proceeds to step S15 of the flow of FIG. 10.

When the control unit 50 determines that the determination value V is not included in the fifth specified range, that is, $V \leq 0.05$ or $0.3 < V$ (NO in step S60), the control unit 50 determines whether the determination value V is included in a sixth specified range (step S61). The sixth specified range is a range in which the component measurement chip 2 is recognized as being inserted into the component measurement apparatus 1 in an inappropriate mode. The sixth specified range can be appropriately determined according to the specifications and the like of the component measurement apparatus 1 and the component measurement chip 2 in an appropriate mode. In the present embodiment, the sixth specified range is set to more than 0.01 and 0.05 or less. That is, the sixth specified range corresponds to a case in which, with respect to the relative output value (the amount of the received light) before the component measurement chip 2 is inserted into the component measurement apparatus 1, the relative output value (the amount of the received light) after the component measurement chip 2 is inserted into the component measurement apparatus 1 is more than 1% and 5% or less. In addition, the sixth specified range of the present description means a range described as the "fourth specified range" in the scope of claims.

When the control unit 50 determines that the determination value V is included in the sixth specified range, that is, $0.01 < V \leq 0.05$ (YES in step S61), the control unit 50 determines that the component measurement chip 2 is inserted into the component measurement apparatus 1 in an inappropriate mode. In such a case, when the determination value V is within the sixth specified range, the control unit 50 can recognize that at least a part of the optical path is blocked by the component measurement chip 2, that the measurement spot is not correctly located in the optical path, or that the used component measurement chip 2 is erroneously mounted. This determination result is hereinafter also simply referred to as "chip recognition failure" in the present description. In such a case, the control unit 50 determines in step S14 of FIG. 10 that the intensity of received light is not within the normal range (NO in step S14). In such a case, the control unit 50 reports an error, for example, by outputting a buzzer sound from the buzzer unit 59 (step S23). The mode of error reporting may be the same as in the above example. The control unit 50 can detect whether the normal measurement can be executed by reporting an error when there is a possibility that the component measurement chip 2 is inserted in an inappropriate mode in this way.

When the control unit 50 determines that the determination value V is not included in the sixth specified range (NO in step S61), the control unit 50 proceeds to step S60. The control unit 50 may recognize that the component measurement chip 2 is not sufficiently inserted into the chip insertion space S by proceeding to step S60 from step S61. In this way, the control unit 50 repeats steps S60 and S61 until the control unit 50 determines that the determination value V is included in the fifth specified range or the determination value V is included in the sixth specified range.

In the present embodiment, when the determination value V is neither within the fifth specified range nor within the sixth specified range, that is, when V≤0.01 or 0.3<V, the control unit 50 may not make a determination regarding the chip normality recognition or the chip recognition failure. This is because there is a possibility that the component measurement chip 2 is not inserted into the component measurement apparatus 1, and that the component measurement chip 2 is not in an appropriate state for making the determination regarding the chip normality recognition or the chip recognition failure. For example, when the component measurement chip 2 is formed of the light-shielding member except for the portion to be measured, while the component measurement chip 2 is being inserted into the component measurement apparatus 1, the radiation light from the light emitting unit 66 is blocked by the component measurement chip 2. In such a case, the radiation light is blocked, and the light receiving unit 72 is in the state in which no radiation light is received. Therefore, there is a possibility that the relative output value is a value close to 0, and the determination value V is 0.01 or less. However, in such a case, in a stage where the component measurement chip 2 is being inserted, the component measurement chip 2 is not in an appropriate state for making the determination regarding the chip normality recognition or the chip recognition failure. Therefore, in this case, the control unit 50 does not make the determination, and makes the determination when the determination value V is within the fifth specified range or the sixth specified range.

In this way, the control unit 50 according to the present embodiment determines whether the component measurement chip 2 is mounted on (inserted into) the component measurement apparatus 1. Further, the control unit 50 can detect whether the normal measurement can be executed. When the control unit 50 determines that an abnormality may occur, the control unit 50 can inform the operator of the possibility of an abnormality by reporting this fact. Further, by outputting an error in response to the type of the determined abnormality, the control unit 50 can also inform the operator of the type of the error. When the control unit 50 determines the chip recognition failure, the control unit 50 may inform and urge the operator to correctly attach the component measurement chip 2. In this way, according to the component measurement apparatus, the component measurement apparatus set and the information processing method according to the present embodiment, even when the component measurement apparatus 1 and the component measurement chip 2 do not have a mechanical configuration for detecting an abnormality, an abnormality in the component measurement apparatus or the component measurement apparatus set can be determined by the light emitting unit 66 and the light receiving unit 72 used for determining an amount of the component to be measured.

In the example described with reference to FIG. 14, the case in which the control unit 50 executes the determination process based on the absolute output value and the determination process based on the relative output value is described. However, the control unit 50 does not necessarily execute both the determination process based on the absolute output value and the determination process based on the relative output value. For example, the control unit 50 can determine whether the component measurement chip 2 is mounted on (inserted into) the component measurement apparatus 1 and can detect at least a part of the abnormality by executing the determination process based on the relative output value.

In the determination process of the second intensity of received light, the third specified range to the sixth specified range may be determined for each of the first light source 67 to the fifth light source 68d, or may be the same for all of the first light source 67 to the fifth light source 68d. For example, absorption and reflection properties of the measurement reagent 22 may differ depending on the wavelengths λ1 to λ5 of the radiation light emitted from the first light source 67 to the fifth light source 68d. Therefore, for example, by applying the third specified range to the sixth specified range that are different depending on the light absorption rate of the measurement reagent 22, the control unit 50 can more accurately determine an abnormality according to a property of the radiation light.

In the determination process of the second intensity of received light, when the output value from the AD converter is within the predetermined range (the third specified range to the sixth specified range) for a predetermined period of time, the control unit 50 may determine that conditions are satisfied (that is, a case of YES in each branch of the flow of FIG. 14). The predetermined period of time may be determined, for example, by a predetermined time. In this case, the predetermined period of time is set to, for example, 3 seconds. The predetermined period of time may be determined, for example, by the number of times of light emission from the first light source 67 to the fifth light source 68d. In this case, the predetermined period of time is determined as, for example, time for 3 times (that is, 3 consecutive combinations) of the combination of the output of the set of emission processes for 16 times and the stop of the output of the radiation light. In this way, because the predetermined period of time for determination is set in the determination process of the second intensity of received light, when the output value from the AD converter is temporarily within the predetermined range due to a certain factor other than the insertion of the component measurement chip 2, it is easy to prevent the control unit 50 from erroneously determining that the component measurement chip 2 is mounted on the component measurement apparatus 1.

Further, in a case in which the predetermined period of time is determined by the number of times of light emission from the first light source 67 to the fifth light source 68d, when the light receiving unit 72 first detects light reception after no radiation light is received in step S13, the control unit 50 may change an interval of executing the combination of the output of the set of emission processes for 16 times and the stop of the output of the radiation light. In particular, the control unit 50 may shorten the interval of executing the combination of the output of the set of emission processes for 16 times and the stop of the output of the radiation light.

For example, as described above, when the combination of the output of the set of emission processes for 16 times and the stop of the output of the radiation light is executed every second in step S11, the control unit 50 may shorten the interval of executing the combination to 0.5 seconds. Accordingly, it is possible to shorten the interval of executing the combination of the output of the set of emission processes for 16 times and the stop of the output of the radiation light, and it is easy to determine a result of the determination process of the second intensity of received light at an earlier stage.

FIG. 15 is a diagram schematically showing the intensities of received light of the radiation light emitted from the first light source 67 to the fifth light source 68d, which are measured by the light receiving unit 72, and is a diagram schematically and mainly showing the intensities of received light measured by the light receiving unit 72 in step S13 to step S16, or step S14 to step S16 of FIG. 10. In FIG. 15, the horizontal axis represents the time and the vertical axis represents the intensity of received light. FIG. 15 shows the intensity of received light measured by the light receiving unit 72, for example, after the determination of YES in step S12 of FIG. 10.

For example, when the operator starts to insert the component measurement chip 2 into the chip mounting space S of the component measurement apparatus 1, the radiation light emitted from the first light source 67 to the fifth light source 68d is blocked by the member constituting the component measurement chip 2. In this case, as shown at times $t_1$ to $t_2$ in FIG. 15, the light receiving unit 72 is in a state of not receiving the radiation light.

When the component measurement chip 2 is mounted on the component measurement apparatus 1 at the time $t_2$, the light receiving unit 72 receives the light transmitted through the measurement reagent 22 of the radiation light emitted from the first light source 67 to the fifth light source 68d (a time $t_3$ in FIG. 15). As schematically shown in FIG. 15, the intensity of received light in the light receiving unit 72 is smaller than that before the component measurement chip 2 is mounted. Further, the degree of change in the intensity of received light before and after mounting the component measurement chip 2 is different for each of the first light source 67 to the fifth light source 68d.

When the light transmitted through the measurement reagent 22 is received at the time $t_3$, the control unit 50 shortens the interval of executing the combination of the output of the set of emission processes for 16 times and the stop of the output of the radiation light from 1 second to 0.5 seconds. Then, when the control unit 50 determines that the component measurement chip 2 is mounted on (inserted into) to the component measurement apparatus 1 and the normal measurement can be executed by executing the determination process of the second intensity of received light, the control unit 50 proceeds to step S15 in FIG. 10.

Referring back to FIG. 10, when the control unit 50 determines that the intensity of received light in the light receiving unit 72 is within the predetermined range (YES in step S14), the control unit 50 adjusts the amount of the radiation light emitted from the light emitting unit 66. In a state in which the mounting of the component measurement chip 2 is completed, the control unit 50 adjusts the amount of the radiation light emitted from the light emitting unit 66 by adjusting currents supplied to the first light source 67 to the fifth light source 68d (step S15). The control unit 50 adjusts the amount of the radiation light such that the amount of the radiation light has a predetermined intensity used in the measurement of the component to be measured. The predetermined intensity used in the measurement of the component to be measured may be appropriately determined according to a specification or the like of the light receiving unit 72, and it is desirable that the predetermined intensity is an intensity that can ensure measurement resolution required for the measurement of the component to be measured.

Specifically, the control unit 50 increases the currents supplied to the first light source 67 to the fifth light source 68d. The amount of the radiation light emitted from the first light source 67 to the fifth light source 68d increases by increasing the currents supplied to the first light source 67 to the fifth light source 68d. More specifically, the control unit 50 adjusts the currents supplied to the first light source 67 to the fifth light source 68d so as to increase the intensities of received light of the radiation light from the first light source 67 to the fifth light source 68d in the light receiving unit 72. In particular, the control unit 50 preferably adjusts the currents supplied to the first light source 67 to the fifth light source 68d such that the intensities of received light of the radiation light from the first light source 67 to the fifth light source 68d in the light receiving unit 72 are intensities suitable for executing the component measurement process described with reference to FIG. 9.

The control unit 50 can adjust the currents supplied to the first light source 67 to the fifth light source 68d, respectively. The control unit 50 can adjust the currents supplied to the first light source 67 to the fifth light source 68d so that the intensities of received light of the radiation light from the first light source 67 to the fifth light source 68d in the light receiving unit 72 are uniform. The uniform intensity of received light here includes not only a predetermined intensity of received light but also an intensity of received light within a width of a predetermined range from the predetermined intensity of received light. For example, the control unit 50 adjusts the currents supplied to the first light source 67 to the fifth light source 68d such that the output value of the intensity of received light in the light receiving unit 72 from the AD converter is an approximately constant value. In this case, for example, the output value of the intensity of received light from the AD converter (12 bits) can be treated as uniform in a range of 3300±50. By adjusting the currents in this way, the measurement resolution of the light receiving unit 72 is improved, and it is easier to perform more accurate component measurement. For example, even if the amount of the radiation light from the first light source 67 to the fifth light source 68d fluctuates with a change in an environmental temperature, such a current adjustment can restrict an effect of the fluctuation. Although a 12-bit AD converter is used in the present embodiment, the same output value can be set depending on the resolution.

In step S15, the control unit 50 may determine an amount of the currents supplied to the first light source 67 to the fifth light source 68d based on a temperature measured by the temperature measurement unit 53. Accordingly, it is easier to restrict the fluctuation in the amount of the radiation light due to the temperature.

Further, in step S15, when the control unit 50 adjusts the currents supplied to the first light source 67 to the fifth light source 68d such that the output value of the intensity of received light in the light receiving unit 72 from the AD converter is a predetermined value (for example, 3300), the control unit 50 may determine that an abnormality in the component measurement apparatus 1 occurs and report this fact with a buzzer sound when the supplied currents exceed a predetermined current threshold value (for example, 15 mA) before the output value of the intensity of received light in the light receiving unit 72 from the AD converter reaches the predetermined value.

Referring to FIG. 15, as schematically shown after a time $t_4$, in step S15, the currents supplied to the first light source 67 to the fifth light source 68d are amplified, and the intensity of received light received by the light receiving unit 72 increases. That is, power consumption can be reduced by increasing the amount of light of the light sources after the measurement chip 2 is correctly mounted.

Referring back to FIG. 10, the control unit 50 acquires a reference intensity of received light after adjusting the currents supplied to the first light source 67 to the fifth light source 68d in step S15 (step S16). The reference intensity of received light is an output value of the intensity of received light in the light receiving unit 72 from the AD converter at a specific time point after step S15 is executed. The reference intensity of received light is preferably acquired immediately after step S15 is executed. The reference intensity of received light is used in a determination process of a third intensity of received light in step S19 to be described below.

The control unit 50 causes the first light source 67 to the fifth light source 68d to continuously emit light (step S17). Specifically, the control unit 50 continuously executes the set of emission processes shown in FIG. 11. In this way, the pulsed light is emitted from the first light source 67 to the fifth light source 68d, for example, every 1 msec. The control unit 50 continues outputting such pulsed light until the control unit 50 determines that the sample and the measurement reagent 22 came into contact with each other in step S19 to be described below.

FIG. 16 is a diagram schematically showing the intensities of received light of the radiation light emitted from the first light source 67 to the fifth light source 68d, which are measured by the light receiving unit 72, and is a diagram schematically and mainly showing the intensity of received light measured by the light receiving unit 72 after step S17 of FIG. 10 is executed. As illustrated in FIG. 16, the pulsed light is continuously emitted from the first light source 67 to the fifth light source 68d, and the light receiving unit 72 receives the pulsed light. By causing the first light source 67 to the fifth light source 68d to continuously emit light in this way, it is possible to improve time resolution of the determination to be executed based on the confirmation of the third intensity of received light in step S19 to be described below.

The control unit 50 calculates a moving average of the intensity of received light received by the light receiving unit 72 in the state in which the first light source 67 to the fifth light source 68d continuously emit light in step S17 (step S18). The control unit 50 can calculate a moving average of the intensities of received light of an appropriate amount of the pulsed light, and for example, can calculate a moving average of the intensities of received light of the pulsed light from five light sources. It is preferable that the control unit 50 calculates the moving average of the intensity of received light of the pulsed light for each light source. In the present embodiment, at least a moving average of an intensity of received light of pulsed light of the fourth predetermined wavelength $\lambda 4$ (520 nm) to be used in the next step S19 is calculated. The control unit 50 may calculate a moving average of an intensity of received light of pulsed light of the third predetermined wavelength $\lambda 3$ (940 nm) in addition to the fourth predetermined wavelength $\lambda 4$. In this case, blood having a hematocrit value in a wide range can be measured.

Next, the control unit 50 executes the determination process of the third intensity of received light (step S19). The determination process of the third intensity of received light is a process for determining two matters. The first matter is to determine whether there is a possibility of an incorrect selection of the processing mode, and the second matter is to determine whether to start the component measurement.

Specifically, in the present embodiment, the control unit 50 determines whether the sample reached the measurement reagent 22 using the reference intensity of received light acquired in step S16, and the moving average of the intensity of received light of the pulsed light of the third predetermined wavelength $\lambda 3$ and the moving average of the intensity of received light of the pulsed light of the fourth predetermined wavelength $\lambda 4$ calculated in step S18. In the present embodiment, in step S19, the control unit 50 determines that the sample reached the measurement reagent 22 when the moving average of the intensity of received light of the pulsed light of the third predetermined wavelength $\lambda 3$ received by the light receiving unit 72 is higher than the reference intensity of received light by a first determination threshold value or more. The first determination threshold value can be appropriately determined. For example, the first determination threshold value can be 101.3% of the reference intensity of received light. In the present embodiment, in step S19, the control unit 50 determines that the sample reached the measurement reagent 22 when the moving average of the intensity of received light of the pulsed light of the fourth predetermined wavelength $\lambda 4$ received by the light receiving unit 72 is lower than the reference intensity of received light by a second determination threshold value or more. The second determination threshold value can be appropriately determined. For example, the second determination threshold value can be 98.5% of the reference intensity of received light.

Here, in the present embodiment, the reason why the radiation light of two different wavelengths, the third predetermined wavelength $\lambda 3$ and the fourth predetermined wavelength $\lambda 4$, is used in the determination process of the third intensity of received light will be described. The sample used for the component measurement apparatus 1 according to the present embodiment may be whole blood or blood plasma. However, properties such as the absorbance with respect to the radiation light of each of the wavelengths are different in the case in which the sample is the whole blood and in the case in which the sample is the blood plasma. However, as in the component measurement apparatus 1 according to the present embodiment, by using the radiation light of the two different wavelengths, the third predetermined wavelength $\lambda 3$ and the fourth predetermined wavelength $\lambda 4$, it is possible to detect that the sample reached the measurement reagent 22 regardless of whether the whole blood or the blood plasma is used as the sample.

For example, when the sample is the whole blood, the sample contains erythrocytes. When the whole blood containing erythrocytes is irradiated with the radiation light of the third predetermined wavelength $\lambda 3$ (940 nm), a refractive index of the whole blood is larger than a refractive index of air, and thus a difference in the refractive index from the member of the component measurement chip 2 containing the measurement reagent 22 is reduced. Although the transmitted light transmitted through the measurement reagent 22 increases and the intensity of received light in the light receiving unit 72 increases, the radiation light is scattered by the erythrocytes and thus the intensity of received light in the light receiving unit 72 is reduced. Thus, the increase and decrease in the intensity of received light is offset by the increase in the intensity of received light caused by the refractive index and the decrease in the intensity of received light caused by the scattering due to the erythrocytes. Therefore, when the sample is the whole blood, it may not be possible to detect that the sample reached the measurement reagent 22 using the radiation light of the third predetermined wavelength λ3 (940 nm).

In contrast, when the whole blood is irradiated with the radiation light of the fourth predetermined wavelength λ4 (520 nm), similar to the case in which the whole blood is irradiated with the radiation light of the third predetermined wavelength λ3, the increase in the intensity of received light caused by the refractive index and the decrease in the intensity of received light caused by the scattering due to the erythrocytes occur. However, when the whole blood is irradiated with the radiation light of the fourth predetermined wavelength λ4, because hemoglobin has a property of easily absorbing light of the fourth predetermined wavelength λ4, the radiation light is largely absorbed by hemoglobin, and the intensity of received light in the light receiving unit 72 is reduced. In addition, more light in a band of the fourth predetermined wavelength λ4 is absorbed and the intensity of received light in the light receiving unit 72 is reduced by reacting glucose contained in the whole blood with the measurement reagent 22 to develop a color. Therefore, in the case in which the whole blood is irradiated with the radiation light of the fourth predetermined wavelength λ4 (520 nm), when the sample reaches the measurement reagent 22, the intensity of received light received by the light receiving unit 72 is reduced due to the effect of absorbing the radiation light of the fourth predetermined wavelength λ4. Thus, when the sample is the whole blood, it is possible to detect that the sample reached the measurement reagent 22 by the fourth predetermined wavelength λ4.

On the other hand, when the sample is the blood plasma, the sample does not contain the erythrocytes or hemoglobin. When the blood plasma containing no erythrocytes or hemoglobin is irradiated with the radiation light of the fourth predetermined wavelength λ4 (520 nm), a refractive index of the blood plasma is larger than the refractive index of air, and thus a difference in the refractive index from the member of the component measurement chip 2 containing the measurement reagent 22 is reduced. Although the transmitted light transmitted through the measurement reagent 22 increases and the intensity of received light in the light receiving unit 72 increases, the light in the band of the fourth predetermined wavelength λ4 is absorbed and the intensity of received light in the light receiving unit 72 is reduced by reacting glucose contained in the blood plasma with the measurement reagent 22 to develop a color. Thus, the increase and decrease in the intensity of received light is offset by the increase in the intensity of received light caused by the refractive index and the decrease in the intensity of received light caused by color development. Therefore, when the sample is the blood plasma, it may not be possible to detect that the sample came into contact with the measurement reagent 22 using the radiation light of the fourth predetermined wavelength λ4 (520 nm).

In contrast, when the blood plasma is irradiated with the radiation light of the third predetermined wavelength λ3 (940 nm), similar to the case in which the blood plasma is irradiated with the radiation light of the fourth predetermined wavelength λ4, the increase in the intensity of received light caused by the refractive index occurs. On the other hand, light in a band of the third predetermined wavelength λ3 is hardly absorbed even if glucose contained in the blood plasma reacts with the measurement reagent 22 to develop a color. Therefore, when the blood plasma is irradiated with the radiation light of the third predetermined wavelength λ3 (940 nm), the effect of increasing the intensity of received light caused by the refractive index has a great influence, so that the intensity of received light received by the light receiving unit 72 increases. Therefore, when the sample is the blood plasma, it is possible to detect that the sample reached the measurement reagent 22 by the third predetermined wavelength λ3.

According to the above principle, the control unit 50 can determine whether the sample reached the measurement reagent 22 when the sample is the blood plasma by determining whether the intensity of received light of the third predetermined wavelength λ3 is increased as compared with the reference intensity of received light, and the control unit 50 can determine whether the sample reached the measurement reagent 22 when the sample is the whole blood by determining whether the intensity of received light of the fourth predetermined wavelength λ4 is reduced as compared with the reference intensity of received light. As described above, according to the present embodiment, it is possible to detect that the sample reached the measurement reagent 22 regardless of whether the sample is the whole blood or the blood plasma. Further, according to the present embodiment, it is possible to detect that the sample reached the measurement reagent 22 even if it is unclear whether the sample is the whole blood or the blood plasma.

The component measurement apparatus 1 according to the present embodiment is capable of executing a process in any one of two processing modes including a first mode of measuring the component to be measured and a second mode of confirming the performance of the component measurement apparatus 1. The operator uses the whole blood or the blood plasma as the sample when the process is executed in the first mode. The operator uses the solution dedicated for the second mode (a control solution) as the sample when the process is executed in the second mode.

The control solution is an aqueous solution of the substance to be measured, and is an aqueous glucose solution. The concentration of glucose in the control solution is appropriately selected from, for example, 30 to 300 mg/dL. A thickening agent, a buffer, a surfactant, and a pigment component imitating a blood color may be added to the control solution. The control solution according to the present embodiment is prepared to be colorless and transparent in consideration of a temporal change of the pigment component. Therefore, because the control solution is colorless and transparent, when the control solution is used as a sample, the control solution exhibits the same properties as the blood plasma described by the above principle. That is, when the control solution is used, it is not possible to detect that the solution comes in contact with the measurement reagent 22 by the radiation light of the fourth predetermined wavelength λ4. However, it is possible to detect that the solution reaches the measurement reagent 22 by the radiation light of the third predetermined wavelength λ3.

The control unit 50 can distinguish the whole blood from the control solution (or the blood plasma) as the sample by such a property, and thus the first matter (whether the selection of the processing mode is correct) and the second matter (whether to start the component measurement) can be determined. That is, in the component measurement apparatus 1, the component measurement apparatus set 100, and the information processing apparatus according to the invention, the sample can be distinguished using light of a shortest wavelength and light of a longest wavelength among a plurality of wavelengths used to detect the component to be measured.

Here, details of the determination process of the third intensity of received light executed by the control unit 50 in step S19 will be described. FIG. 17 is a flowchart showing an example of the determination process of the third intensity of received light. As described above, in the present embodiment, it is assumed that the operator selects the first mode of measuring the component to be measured as the processing mode when the flow of FIG. 10 is started. Alternatively, it is assumed that the first mode is set as an initial setting of the control unit 50.

The control unit 50 determines whether there is a possibility of an incorrect processing mode selected by the operator by steps S71 and S72. Specifically, first, the control unit 50 determines whether the moving average calculated in step S18 of FIG. 10 reaches the first determination threshold value (step S71).

When the control unit 50 determines that the moving average of the intensity of received light with respect to the radiation light of the third predetermined wavelength λ3 does not reach the first determination threshold value (NO in step S71), the control unit 50 determines whether the moving average calculated in step S18 of FIG. 10 reaches the second determination threshold value (step S72).

When the control unit 50 determines that the moving average of the intensity of received light with respect to the radiation light of the fourth predetermined wavelength λ4 does not reach the second determination threshold value (NO in step S72), the control unit 50 determines in step S19 of FIG. 10 that a difference between the intensity of received light received by the light receiving unit 72 and the reference intensity of received light does not exceed a predetermined value (NO in step S19). In such a case, the control unit 50 proceeds to step S18 and calculates the moving average again.

When the control unit 50 determines in step S71 that the moving average of the intensity of received light with respect to the radiation light of the third predetermined wavelength λ3 reaches the first determination threshold value (YES in step S71), the control unit 50 performs output to the operator of the component measurement apparatus 1 to confirm whether the selection of the processing mode is correct (step S73). The output for confirming whether the selection of the processing mode is correct can be executed in various methods. For example, the output for confirming whether the selection of the processing mode is correct can be executed by being by displayed on the display unit 11.

Here, as described above, in the present embodiment, the operator selects the first mode of measuring the component to be measured as the processing mode. Alternatively, the first mode is selected as the initial setting. That is, it is considerable that the whole blood may be used as the sample. However, the fact that the moving average of the intensity of received light with respect to the radiation light of the third predetermined wavelength λ3 reaches the first determination threshold value means that the control solution or the blood plasma may be used as the sample instead of the whole blood. Therefore, in step S73, it is possible to urge the operator to confirm whether to continue the process in the first mode by performing the output for confirming whether the selection of the processing mode is correct. Accordingly, the number of times of input process regarding the processing mode by the operator can be reduced by distinguishing the whole blood which is most frequently measured from the sample other than the whole blood.

Further, when it is determined that the set processing mode is incorrect, the measurement process may be performed in the other correct processing mode.

The operator who confirms the output in step S73 (for example, display on the display unit 11) re-inputs whether to execute the process in any one of the processing modes including the first mode and the second mode. The control unit 50 receives an input of the operator regarding the processing mode (step S74).

When the control unit 50 receives an input indicating that the process is executed in the first mode (the first mode in step S74), the control unit 50 determines to execute the process in the first mode. In this case, because it is determined in step S71 that the moving average of the intensity of received light with respect to the radiation light of the third predetermined wavelength λ3 reaches the first determination threshold value, according to the above principle, it can be said that the sample reaches the measurement reagent 22 (the reaction starts). Therefore, in this case, the control unit 50 determines in step S19 of FIG. 10 that the difference between the intensity of received light received by the light receiving unit 72 and the reference intensity of received light exceeds the predetermined value (YES in step S19), the control unit 50 proceeds to step S20 and starts the processes of steps S20 to S22 as the process in the first mode.

For example, when the blood plasma instead of the whole blood is used as the sample, because the moving average of the intensity of received light with respect to the radiation light of the third predetermined wavelength λ3 reaches the first determination threshold value, the confirmation regarding whether the selection of the processing mode is correct is output in step S73 even if the selection of the first mode input by the operator is correct. In this case, the operator can execute the process in the first mode by an input of selecting the first mode.

On the other hand, when the control unit 50 receives an input indicating that the process is executed in the second mode (the second mode in step S74), the control unit 50 executes the process in the second mode. The process in the second mode is a process of confirming the performance of the component measurement apparatus 1. As the process in the second mode, for example, the measurement process corresponding to the measurement of the control solution is performed, a measurement result is calculated, and a fact that the control solution was measured is displayed on the display unit 11.

An example is shown that in step S73, the input from the operator is received in step S74 after the operator confirms whether the selection of the processing mode is correct, the present disclosure is not limited to this example. For example, even when YES is determined in step S71, the control unit 50 executes the process in the first mode (proceeds to step S20) and executes the process until the acquisition of the actual measurement value is completed (up to step S22), and then receives the selection of the processing mode. More specifically, when the input of the processing mode by the operator in steps S73 and S74 is not executed for a certain time, or when the component measurement chip 2 continues being mounted on the component measurement apparatus 1 over a predetermined time (for example, 10 seconds), it may be considered that the process in the first mode is selected in the reception of the input mode in step S74. Accordingly, an incorrect actual measurement value due to the excessive progress of the color reaction of the reagent in the component measurement chip 2 while the processing mode is received in step S74 can be prevented.

Alternatively, when a predetermined time elapses after the confirmation regarding whether the selection of the processing mode is correct is output in step S73, the process in the first mode may be continued without executing step S74. More specifically, when the input of the processing mode by the operator in step S74 is not executed for a certain time, or when the component measurement chip continues being mounted on the component measurement apparatus 1 over a predetermined time (for example, 10 seconds), it may be considered that the process in the first mode is selected in the reception of mode input in step S74. Further, an appropriate calculation process may be automatically changed according to switching between the first mode and the second mode.

When the control unit 50 determines in step S72 that the moving average of the intensity of received light with respect to the radiation light of the fourth predetermined wavelength λ4 reaches the second determination threshold value (YES in step S72), the control unit 50 determines in step S19 of FIG. 10 that the difference between the intensity of received light received by the light receiving unit 72 and the reference intensity of received light exceeds the predetermined value (Yes in step S19), the control unit 50 proceeds to step S20 and starts the processes of steps S20 to S22 as the process in the first mode. When the control unit 50 determines in step S72 that the moving average of the intensity of received light with respect to the radiation light of the fourth predetermined wavelength λ4 reaches the second determination threshold value (YES in step S72), it can be said that the use of the whole blood as the sample can be confirmed, and thus it can be said that the input indicating that the process is executed in the first mode is correct. Therefore, in this case, the process in the first mode can be executed without the operator confirming whether the selection of the processing mode is correct.

In the present embodiment, in the determination of the third intensity of received light, the reference intensity of received light is compared with the moving average at the third predetermined wavelength λ3 and the moving average at the fourth predetermined wavelength λ4. By using the moving average in this way, it is easy to prevent the control unit 50 from mistakenly determining that the sample and the measurement reagent 22 came into contact with each other when the intensity of received light temporarily increases or decreases due to a certain factor other than the contact between the sample and the measurement reagent 22.

In step S19, the control unit 50 may further set a threshold value for determining whether the component measurement chip 2 is detached from the component measurement apparatus 1. For example, when the component measurement chip 2 is extracted from the chip mounting space S, similar to the case in which the component measurement chip 2 is inserted, at least a part of the radiation light emitted from the first light source 67 to the fifth light source 68d does not reach the light receiving unit 72 due to the member constituting the component measurement chip 2. Therefore, the control unit 50 may determine that the component measurement chip 2 is detached from the component measurement apparatus 1 when, for example, a relative output value of the intensity of received light from the AD converter is smaller than the predetermined threshold value. At this time, for example, a buzzer sound may be output from the buzzer unit 59 to report an error. When the component measurement chip 2 is completely extracted from the component measurement apparatus 1, the radiation light emitted from the first light source 67 to the fifth light source 68d is directly applied to the light receiving unit 72, and the intensity of received light in the light receiving unit 72 is increased. Therefore, the control unit 50 may determine that the component measurement chip 2 is detached from the component measurement apparatus 1 when, for example, the relative output value of the intensity of received light from the AD converter is larger than the predetermined threshold value. At this time, for example, a buzzer sound may be output from the buzzer unit 59 to report an error.

When the control unit 50 determines that the difference between the intensity of received light received by the light receiving unit 72 and the reference intensity of received light exceeds the predetermined value (YES in step S19), the control unit 50 determines an initial value of the intensity of received light received by the light receiving unit 72 (step S20) as the process in the first mode. The initial value (reference value) is an actual measurement value of the absorbance of the radiation light onto the mixture X at a specific time before the sample reaches the measurement reagent 22, that is, the output value of the intensity of received light in the light receiving unit 72 from the AD converter. The control unit 50 can set an output value of the intensity of received light before, by a predetermined time, a time when it is determined in step S19 that the difference between the intensity of received light received by the light receiving unit 72 and the reference intensity of received light exceeds the predetermined value, as the initial value. The predetermined time can be appropriately set, for example, 0.5 seconds. The shorter the predetermined time, an output value under a condition closer to a condition (for example, a surrounding environment) after the sample reaches the measurement reagent 22 can be set as the initial value. For example, when the first light source 67 to the fifth light source 68d continuously emit light, temperature of the first light source 67 to the fifth light source 68d may rise and the amount of the emitted radiation light may change. However, by shortening the predetermined time, acquisition conditions of an actual measurement value to be acquired in the next step S21 and the output value can be close to each other. In this way, by determining the initial value after determining that the sample reached the measurement reagent 22, an output value immediately before the sample reaches the measurement reagent 22 can be set as the initial value (the reference value), and an actual measurement value can be derived.

In addition, when the control unit 50 determines that the sample reached the measurement reagent 22, the control unit 50 starts to acquire the actual measurement value of the absorbance of the radiation light onto the mixture X, which is used for measuring the component to be measured (step S21). The actual measurement value corresponds to the first actual measurement value to the fifth actual measurement value in the flow of FIG. 9. In this way, when the control unit 50 determines that the sample containing the component to be measured started the color reaction with the measurement reagent 22, the control unit 50 can automatically start the acquisition of the actual measurement value. Therefore, the component measurement apparatus 1 increases the usability.

The control unit 50 ends the acquisition of the actual measurement value after a predetermined time from the start of the acquisition of the actual measurement value in step S21 (step S22). At this time, the control unit 50 may stop the light emission from the first light source 67 to the fifth light source 68d. The predetermined time can be appropriately set according to the properties of the measurement reagent 22 and the like, and can be set, for example, to 9 seconds. In this way, the control unit 50 ends the emission process of the radiation light executed in the component measurement process.

The control unit 50 can measure the concentration of glucose in the sample by using the acquired actual measurement value and executing the component measurement method described in the present embodiment. Although in the above embodiment, a method for measuring the concentration of glucose when the sample is the whole blood is described, the concentration of glucose can be measured by the same method when the sample is the blood plasma.

FIG. 18 is a diagram schematically showing the intensities of received light of the radiation light emitted from the first light source 67 to the fifth light source 68*d*, which are measured by the light receiving unit 72, and is a diagram schematically and mainly showing the intensities of received light measured by the light receiving unit 72 in step S18 to step S21 in FIG. 10. In FIG. 18, the horizontal axis represents the time and the vertical axis represents the intensity of received light.

The control unit 50 calculates the moving average of the intensity of received light received by the light receiving unit 72 while the first light source 67 to the fifth light source 68*d* continuously emit light in step S17 (step S18). The control unit 50 executes the determination process of the third intensity of received light in step S19. The control unit 50 repeats steps S18 and S19 until the control unit 50 determines that the difference between the intensity of received light received by the light receiving unit 72 and the reference intensity of received light exceeds the predetermined value (until a time $t_6$ in FIG. 18) in the determination process of the third intensity of received light.

When the control unit 50 determines that the difference between the intensity of received light received by the light receiving unit 72 and the reference intensity of received light exceeds the predetermined value (YES in step S19) at the time $t_6$, the control unit 50 determines the initial value of the intensity of received light received by the light receiving unit 72 (step S20). For example, the control unit 50 determines, as the initial value, the output value of the intensity of received light from the AD converter at the time $t_5$ that is 0.5 seconds before the time $t_6$. Further, the control unit 50 starts to acquire the actual measurement value from the time $t_6$ (step S21). The control unit 50 ends the acquisition of the actual measurement value after the predetermined time elapsed (step S22). In addition, when there is a possibility that the second mode is selected (YES in step S71) and no processing mode is input in step S73, the acquired initial value and the actual measurement value may be stored in the memory, the input of the processing mode may be confirmed, and then a measurement value may be calculated and displayed according to the processing mode.

The component measurement apparatus, the component measurement apparatus set and the information processing apparatus according to the invention are not limited to the specific descriptions of the embodiments described above, and various changes can be made without departing from a scope of the invention described in the claims. In the embodiments described above, the concentration of glucose is measured for the measurement of glucose as a component to be measured. However, the measurement of glucose is not limited to the concentration; rather, another physical quantity may be measured. Further, in the embodiments described above, glucose in the blood plasma component is exemplified as the component to be measured in blood. However, the component to be measured is not limited to glucose; for example, cholesterol, saccharides, ketones, uric acid, hormones, nucleic acids, antibodies, and antigens in blood can also be used as the component to be measured. Therefore, the component measurement apparatus is not limited to the blood glucose level measurement apparatus. Further, in the embodiments described above, a light receiving unit 72 that receives the transmitted light transmitted through the component measurement chip 2 is used; however, a light receiving unit that receives the reflected light reflected from the component measurement chip 2 may be used.

In the embodiment described above, regarding the process of determining whether there is the possibility of an incorrect selection of the processing mode, when the operator selects the first mode as the processing mode in advance and the control unit 50 determines that the process in the second mode may be appropriate (that is, determines that the moving average of the intensity of received light with respect to the radiation light of the third predetermined wavelength λ3 reaches the first determination threshold value), the operator confirms whether the selection of the processing mode is correct. However, the process of determining whether there is the possibility of an incorrect selection of the processing mode is not limited thereto. For example, when the operator selects the second mode as the processing mode in advance and the control unit 50 determines that the process in the first mode may be appropriate (that is, determines that the moving average of the intensity of received light with respect to the radiation light of the fourth predetermined wavelength λ4 reaches the second determination threshold value), the operator may confirm whether the selection of the processing mode is correct. In this way, based on whether the difference between the reference intensity of received light and the intensity of received light is higher than the reference intensity of received light by the first determination threshold value or more, or is lower than the reference intensity of received light by the second determination threshold value or more, the control unit 50 may determine whether the sample is used in the processing mode selected based on the input operation. When the sample is not used in the processing mode selected based on the input operation, the control unit 50 determines that there is a possibility of an incorrect selection of the processing mode.

In the embodiment described above, the control unit 50 outputs a request to confirm whether the selection of the processing mode is correct, receives the input regarding the processing mode by the operator, and executes the process in the input processing mode. However, the control unit 50 does not necessarily execute the process after receiving the input. For example, the control unit 50 may automatically select the processing mode and execute the process after executing the processes of steps S71 and S72. That is, when the control unit 50 determines that there is a possibility of an incorrect selection of the processing mode, the control unit 50 may automatically select the other processing mode that is not selected and execute the process in the other processing mode.

Alternatively, regardless of whether the operator selects the first mode or the second mode in advance, the control unit 50 may determine whether there is a possibility of an incorrect selection of the processing mode when the moving average of the intensity of received light reaches the first determination threshold value or the second determination threshold value. In this case, regardless of whether the operator selects the first mode or the second mode in advance, when the moving average of the intensity of received light reaches the first determination threshold value or the second determination threshold value, the output for confirming whether the selection of the processing mode is correct may be performed. Alternatively, in this case, when the operator determines a possibility of an incorrect selection of the processing mode based on the determination result of whether there is a possibility of an incorrect processing mode selection, the operator may be informed. Alternatively, when the operator selects the second mode in advance, the control unit 50 may automatically switch to the first mode and perform the process (the measurement processing of the sample) in the first mode in a stage where the moving average of the intensity of received light exceeds the second determination threshold value.

As another embodiment, the first mode and the second mode may be selected by operating a terminal (smartphone or the like) linked with the component measurement apparatus 1. In particular, when the component measurement apparatus does not include an input button, the component measurement apparatus 1 may be set from the terminal.

REFERENCE CHARACTER LIST

1: component measurement apparatus
2: component measurement chip
10: housing
10a: main body portion
10b: chip mounting portion
11: display unit
12: removal lever
13: power button
14: operation button
21: base member
22: measurement reagent
23: flow path
23a: gap
24: supply portion
25: cover member
26: eject pin
50: control unit
51: light measurement unit
52: storage unit
53: temperature measurement unit
54: power supply unit
55: battery
56: communication unit
57: clock unit
58: operation unit
59: buzzer unit
66: light emitting unit
67: first light source
68a: second light source
68b: third light source
68c: fourth light source
68d: fifth light source
69a: first aperture portion
69b: second aperture portion
72: light receiving unit
80: holder member
100: component measurement apparatus set

The invention claimed is:
1. A component measurement apparatus comprising:
a chip insertion space for inserting a component measurement chip provided with a reagent that reacts with a component to be measured in a sample;
a light emitting unit configured to emit radiation light to the component measurement chip in a state in which the component measurement chip is inserted into the chip insertion space;
a light receiving unit configured to receive light transmitted through or reflected from the component measurement chip; and
a control unit capable of executing a process in at least (i) a first mode of measuring the component to be measured in the sample using an actual measurement value of an intensity of received light in the light receiving unit, and (ii) a second mode of confirming performance of the component measurement apparatus using an actual measurement value of an intensity of received light in the light receiving unit, wherein the control unit is configured to:
determine a difference between (i) a reference intensity of received light in the light receiving unit at a specific time point after the component measurement chip is inserted into the chip insertion space, and (ii) the intensity of received light received by the light receiving unit, and
when the difference exceeds a predetermined value, determine that there is a possibility that an incorrect processing mode has been selected for execution.

2. The component measurement apparatus according to claim 1, wherein:
the control unit is configured to:
when a difference between the reference intensity of received light and a moving average value of the intensity of received light received by the light receiving unit exceeds a predetermined value, determine that there is a possibility that the incorrect processing mode has been selected for execution.

3. The component measurement apparatus according to claim 1, wherein:
the control unit is configured to:
when the control unit determines that there is a possibility of the incorrect processing mode, output a request to confirm whether a correct processing mode has been selected for execution.

4. The component measurement apparatus according to claim 1, wherein:
the control unit is configured to:
determine whether the sample is suitable for use in a processing mode based on whether the difference between the reference intensity of received light and the intensity of received light is higher than the reference intensity of received light by a first determination threshold value or more, or is lower than the reference intensity of received light by a second determination threshold value or more.

5. The component measurement apparatus according to claim 4, wherein:
when the control unit determines that the sample is not suitable for use in the processing mode, the control unit determines that there is a possibility that the incorrect processing mode has been selected for execution.

6. The component measurement apparatus according to claim 4, wherein:
the light emitting unit comprises:
a first light source configured to emit radiation light of a first predetermined wavelength to a mixture of the sample and the reagent in order to determine an amount of the component to be measured;
a second light source configured to emit radiation light of a second predetermined wavelength that is used to estimate an amount of noise other than a predetermined coloring component included in an actual measurement value of absorbance of the mixture measured by the radiation light from the first light source, an effect caused by light scattering due to a component contained in the sample being dominant in the radiation light of the second predetermined wavelength; and a third light source configured to emit radiation light of a third predetermined wavelength that is used to estimate the amount of noise, a ratio of absorbance caused by light absorption due to a predetermined component contained in the sample being equal to or greater than a predetermined value in the radiation light of the third predetermined wavelength.

7. The component measurement apparatus according to claim 6, wherein:

the control unit is configured to:

when the first mode is selected as the processing mode to be executed, and a difference between the reference intensity of received light and an intensity of received light with respect to the radiation light of the second predetermined wavelength reaches the first determination threshold value, determine that there is a possibility of an incorrect selection of the processing mode.

8. The component measurement apparatus according to claim 6, wherein:

the control unit is configured to:

when the second mode is selected as the processing mode to be executed and a difference between the reference intensity of received light and an intensity of received light with respect to the radiation light of the third predetermined wavelength 24 reaches the second determination threshold value, determine that there is a possibility of an incorrect selection of the processing mode.

9. The component measurement apparatus according to claim 6, wherein:

the control unit is configured to:

execute the process in the first mode of measuring erythrocytes and hemoglobin contained in the erythrocytes in the sample.

10. The component measurement apparatus according to claim 1, wherein:

when the control unit determines that there is a possibility that the incorrect processing mode has been selected for execution, the control unit executes a process in a processing mode other than the processing mode that has been selected for execution.

11. A component measurement apparatus set comprising:
a component measurement chip; and
a component measurement apparatus comprising:
a chip insertion space for inserting a component measurement chip provided with a reagent that reacts with a component to be measured in a sample,
a light emitting unit configured to emit radiation light to the component measurement chip in a state in which the component measurement chip is inserted into the chip insertion space,
a light receiving unit configured to receive light transmitted through or reflected from the component measurement chip, and
a control unit capable of executing a process in at least (i) a first mode of measuring the component to be measured in the sample using an actual measurement value of an intensity of received light in the light receiving unit, and (ii) a second mode of confirming performance of
the component measurement apparatus using an actual measurement value of an intensity of received light in the light receiving unit, wherein the control unit is configured to:
determine a difference between (i) a reference intensity of received light in the light receiving unit at a specific time point after the component measurement chip is inserted into the chip insertion space, and (ii) the intensity of received light received by the light receiving unit, and
when the difference exceeds a predetermined value, determine that there is a possibility that an incorrect processing mode has been selected for execution.

12. A method of information processing, the method comprising:
providing a component measurement apparatus comprising:
a chip insertion space for inserting a component measurement chip provided with a reagent that reacts with a component to be measured in a sample,
a light emitting unit configured to emit radiation light to the component measurement chip in a state in which the component measurement chip is inserted into
the chip insertion space,
a light receiving unit configured to receive light transmitted through or reflected from the component measurement chip, and
a control unit capable of executing a process in at least (i) a first mode of measuring the component to be measured in the sample using an actual measurement value of an intensity of received light in the light receiving unit, and (ii) a second mode of confirming performance of the component measurement apparatus using an actual measurement value of an intensity of received light in the light receiving unit;
determining, at the control unit, a difference between (i) a reference intensity of received light in the light receiving unit at a specific time point after the component measurement chip is inserted into the chip insertion space, and (ii) the intensity of received light received by the light receiving unit; and
when the difference exceeds a predetermined value, determining, at the control unit, that there is a possibility that an incorrect processing mode has been selected for execution.

* * * * *